United States Patent
Maltz et al.

(10) Patent No.: US 11,596,808 B2
(45) Date of Patent: *Mar. 7, 2023

(54) RADIATION THERAPY SYSTEM

(71) Applicant: SHANGHAI UNITED IMAGING HEALTHCARE CO., LTD., Shanghai (CN)

(72) Inventors: Jonathan Maltz, Walnut Creek, CA (US); Johannes Stahl, Walnut Creek, CA (US); Jian Liu, Shanghai (CN); Jian Zhang, Shanghai (CN); Yuelin Shao, Shanghai (CN); Xiaolong Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 814 days.

This patent is subject to a terminal disclaimer.

(21) Appl. No.: 16/600,985

(22) Filed: Oct. 14, 2019

(65) Prior Publication Data

US 2020/0086143 A1    Mar. 19, 2020

Related U.S. Application Data

(63) Continuation of application No. 14/985,993, filed on Dec. 31, 2015, now Pat. No. 10,441,816.

(51) Int. Cl.
*A61N 5/10* (2006.01)
*A61B 6/10* (2006.01)
*A61B 6/00* (2006.01)

(52) U.S. Cl.
CPC ............ *A61N 5/1049* (2013.01); *A61B 6/102* (2013.01); *A61B 6/4435* (2013.01);
(Continued)

(58) Field of Classification Search
CPC ............ A61N 5/1077–1084; A61B 6/032–037
See application file for complete search history.

(56) References Cited

U.S. PATENT DOCUMENTS 4,112,306 A * 9/1978 Nunan ................... A61N 5/10
976/DIG. 428
4,658,408 A  4/1987 Amor et al.
(Continued)

FOREIGN PATENT DOCUMENTS

CN    102309824 A    1/2012
CN    102440795 A *  5/2012  ........... A61B 6/4417
(Continued)

OTHER PUBLICATIONS

International Search Report in PCT/CN2014/091001 dated Feb. 17, 2015, 2 pages.

*Primary Examiner* — Catherine B Kuhlman
(74) *Attorney, Agent, or Firm* — Metis IP LLC

(57) ABSTRACT

A radiation therapy medical apparatus is disclosed. The medical apparatus comprises: a base; a cylindrical gantry, peripherally and rotatably supported by the base; a radiation therapy assembly, comprising an arm and a radiation head, wherein one end of the arm is fixed to a first position on a first side of the gantry and the other end thereof is extended outwardly, and the radiation head is fixed to the other end of the arm; an imaging assembly, mounted to a second side of the gantry opposite to the first side, and configured to be a first balanced weight part for balancing the radiation therapy assembly; and a counterbalance, fixed to the second side of the gantry, and configured to cooperate with the imaging assembly to prevent the gantry from turnover under action of the radiation therapy assembly and configured to dynamically balance with the radiation therapy assembly with respect to a rotation axis of the gantry.

15 Claims, 19 Drawing Sheets

(52) U.S. Cl.
CPC .... *A61N 5/1081* (2013.01); *A61N 2005/1052* (2013.01); *A61N 2005/1055* (2013.01); *A61N 2005/1061* (2013.01)

(56) References Cited

U.S. PATENT DOCUMENTS

| | | | |
|---|---|---|---|
| 5,047,641 A | | 9/1991 | Besseling et al. |
| 5,175,754 A | | 12/1992 | Casey et al. |
| 6,373,060 B1 | | 4/2002 | Yamakawa et al. |
| 6,385,288 B1 | | 5/2002 | Kanematsu |
| 6,810,103 B1 | * | 10/2004 | Tybinkowski ......... A61B 6/032 250/363.04 |
| 6,842,502 B2 | | 1/2005 | Jaffray et al. |
| 6,914,959 B2 | | 7/2005 | Bailey et al. |
| 7,200,202 B2 | | 4/2007 | Kusch et al. |
| 7,983,380 B2 | | 7/2011 | Guertin et al. |
| 8,218,718 B1 | | 7/2012 | Van Herk et al. |
| 8,989,846 B2 | | 3/2015 | Kuduvalli et al. |
| 9,687,200 B2 | | 6/2017 | Maurer, Jr. |
| 2003/0185338 A1 | | 10/2003 | Dafni et al. |
| 2006/0113482 A1 | | 6/2006 | Pelizzari et al. |
| 2010/0220837 A1 | | 9/2010 | Bressel |
| 2011/0007867 A1 | * | 1/2011 | Fadler ................ A61N 5/1049 378/65 |
| 2016/0287904 A1 | | 10/2016 | Liu et al. |
| 2017/0156688 A1 | * | 6/2017 | Tian ...................... A61B 6/032 |

FOREIGN PATENT DOCUMENTS

| | | |
|---|---|---|
| CN | 102440795 A | 5/2012 |
| CN | 202489969 U | 10/2012 |
| DE | 102011081257 A1 | 2/2013 |
| WO | 2014111869 A2 | 7/2014 |

* cited by examiner

Prior Art

Prior Art

RADIATION THERAPY SYSTEM

CROSS-REFERENCE TO THE RELATED APPLICATIONS

This application is a continuation application of U.S. patent application Ser. No. 14/985,993, filed on Dec. 31, 2015, and the contents of which are incorporated herein by reference.

BACKGROUND

Field

The application relates to a medical apparatus, and more particularly, relates to a medical apparatus for delivering radiotherapy.

Description

Radiotherapy is a method which transmits radioactive rays such as α-rays, β-rays, or γ-rays, generated by radioisotopes, X-rays, electron beams, proton beams or other particles, to diseased tissue (e.g., a cancerous tumor). The rays kill cells of the tissue by causing ionizations within the cells or other cell damage.

A linear accelerator is a particle accelerator commonly used for radiotherapy. A linear accelerator comprises a radiation head in which a radiation source is arranged for radiating a radioactive beam toward diseased tissue. The radiation source may include an accelerating tube, an electron gun, a moving target, a magnetic biasing system, a collimator, and a flattening filter. The radiation head also includes a high-density lead shielding layer to prevent extraneous radioactive rays from harming bystanders during use of the linear accelerator. The above components, and others, contribute to the substantial mass of the radiation head.

Conventional radiotherapy is typically performed in conjunction with a computed tomography (hereinafter, "CT") imaging apparatus or a magnetic resonance (hereinafter, "MR") imaging apparatus to determine a specific position of the diseased tissue and to thereby properly position the diseased tissue relative to the emitted rays of the linear accelerator. As is known in the art, a CT imaging apparatus is particularly suited for imaging bone and an MR imaging apparatus is particularly suited for imaging soft tissue.

In one example, a patient is positioned within an imaging apparatus to image the diseased tissue and refine the patient's position, and the patient is then moved to the linear accelerator to radiate the diseased tissue. Since both the linear accelerator and the imaging apparatus occupy a large volume, the patient is moved over a substantial distance therebetween, thereby complicating the procedure and increasing the risk and extent of positioning errors.

FIG. 19 illustrates a prior combined medical apparatus 100. The medical apparatus 100 comprises a radiation therapy assembly 102, an imaging assembly 104, and a couch assembly 106. More particularly, the radiation therapy assembly 102 is a common radiotherapy apparatus, which comprises a gantry 1022 in which a through-hole 1024 extending along a horizontal direction is defined. One end of an arm 1026 is secured to the gantry 1022 and the other end thereof extends outwardly. A radiation head 1028 is fixed to the other end of the arm 1026. The imaging assembly 104 is a common CT imaging apparatus, which comprises a gantry 1042 defining a through-hole 1044 extending along a horizontal direction. An X-ray tube 1046 and a detector 1048 are arranged oppositely on a rotatable mechanism (not shown) surrounding the through-hole 1044. The couch 106 comprises a base 1062 and a patient support 1064 arranged on the base 1062.

In order to image a patient, the patient is placed on the patient support 1064, and the patient support 1064 is moved through the through-holes 1024 and 1044 in order to position the patient between the X-ray tube 1046 and the detector 1048. The X-ray tube 1046 and the detector 1048 are then operated as is known in the art to acquire an image of the patient. To radiate the patient, the patient support 1064 is moved such that the target volume, determined from the acquired image, is positioned in the beam field of the radiation head.

The length spanned by the through-holes 1024 and 1044 or, more particularly, the distance from the isocenter of the radiation therapy assembly 102 to the imaging plane of the imaging assembly 104, is quite long. The resulting movable distance of the patient support 1064 is directly related to the likelihood that deformation of the couch assembly and/or the patient support will introduce errors in imaging and/or radiation delivery. Additionally, as recited above, the large volume occupied by the combined medical apparatus 100, consisting of the radiation therapy assembly 102 and the imaging assembly 104, poses a significant challenge to any institution (e.g., a hospital) employing the apparatus 100.

FIG. 20 illustrates another prior combined medical apparatus 200. The medical apparatus 200 comprises a radiation therapy assembly 202, an imaging assembly 204 and a couch assembly 206. The radiation therapy assembly 202 comprises a gantry 2021 defining a through-hole 2022 extending along the horizontal direction. One end of an arm 2023 is secured to the gantry 2021 and the other end thereof extends outwardly. A radiation head 2024 is fixed on this other end of the arm 2023. The imaging assembly 204 is a CT imaging assembly which comprises a gantry 2041 defining a through-hole 2042 along the horizontal direction. An X-ray tube 2043 and a detector 2044 are oppositely arranged around through-hole 2042 on a rotatable mechanism (not shown). The couch assembly 206 comprises a base 2061 and a rotatable platform 2062 which is coupled to the base 2061 and rotatable about a vertical axis 2063. A patient support 2064 is slidably secured to the platform 2062, and a patient P is shown positioned on the patient support 2064.

In contrast to the combined medical apparatus 100 as shown in FIG. 19, the radiation therapy assembly 202 and the imaging assembly 204 of the medical apparatus 200 are separately arranged, and the couch assembly 206 is arranged between the radiation therapy assembly 202 and the imaging assembly 204. Accordingly, during the transition between an imaging mode and a radiating mode, the movement of the patient support 2064 differs from the movement of the patient support 1064 as shown in FIG. 19, i.e., the patient support 2064 rotates to change between the two modes but the patient support 1064 translates linearly to change modes.

The movable distance of the patient support 2064 is shorter than that of the patient support 1064 in FIG. 19, and thus, the apparatus 200 attempts to address the problem of flexible deformation of the patient support 2064. However, since the apparatus 200 requires sufficient distance between the radiation therapy assembly 202 and the imaging assembly 204 such that the patient support 2064 can be rotated without interference with the radiation therapy assembly 202 and the imaging assembly 204, the space occupied by the medical apparatus 200 is unsuitably large.

Thus, technical solutions are desired in radiotherapy to reduce complications, increase efficiency of resource usage, and decrease positioning error.

DETAILED DESCRIPTION

The following description is provided to enable any person in the art to make and use the described embodiments and sets forth the best mode contemplated for carrying out the described embodiments. Various modifications, however, will remain readily apparent to those in the art.

The claims are not limited to the embodiments described below. As recited in the present description and claims, the terms 'a', 'an', 'said' and/or 'the' do not specifically refer to singular items but also include plural items unless exceptions are clearly noted in the text. Generally speaking, terms such as 'comprise' and 'include', merely express that an explicit step or element is included but not to the exclusion of other steps or elements. That is, the method or apparatus may include other steps or elements. In addition, 'up', 'down', 'left', 'right', 'front' and 'behind' are merely used for purposes of description in view of orientations shown in the figures and not intended to be limiting.

Some embodiments comprise a radiation therapy medical apparatus comprising a radiation therapy assembly and an imaging assembly connected to a gantry. The gantry defines a through-hole allowing a patient support to pass therethrough. A patient placed on the support can be imaged and then moved to the radiation therapy assembly to perform radiation therapy by directly and linearly moving the patient support. Thus, positioning errors caused by the movement of the patient may be reduced, resulting in increased efficiency of the radiation process. In addition, the imaging assembly connected to the gantry may serve as a counterbalance to the weight of the radiation therapy assembly, so as to reduce volume and weight of the entire medical apparatus. Consequently, a medical apparatus according to some embodiments may also address the technical problems of device stability, integration and/or minimization.

Figure 1:
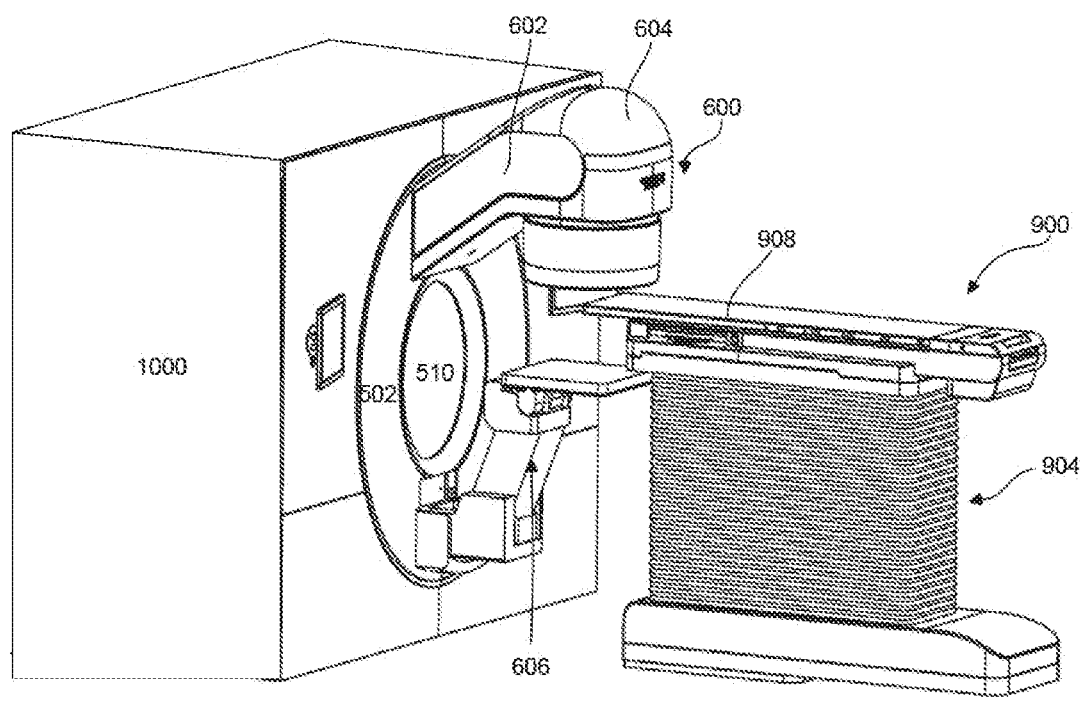
FIG. 1 is a schematic front-side perspective view of a radiation therapy system according to some embodiments.
Figure 2:
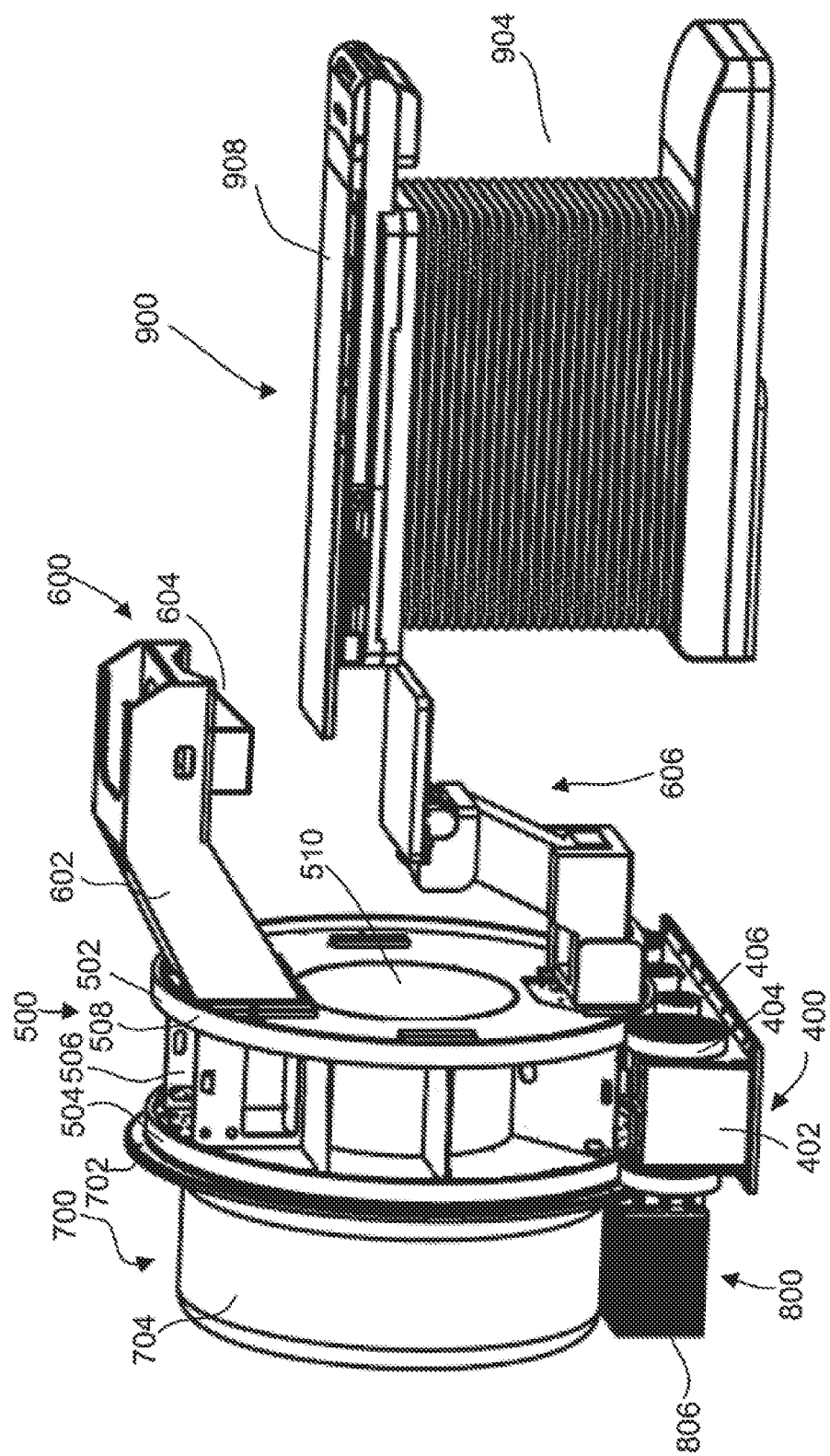
FIG. 2 is a schematic front-side perspective view of a radiation therapy system according to some embodiments.
Figure 3:
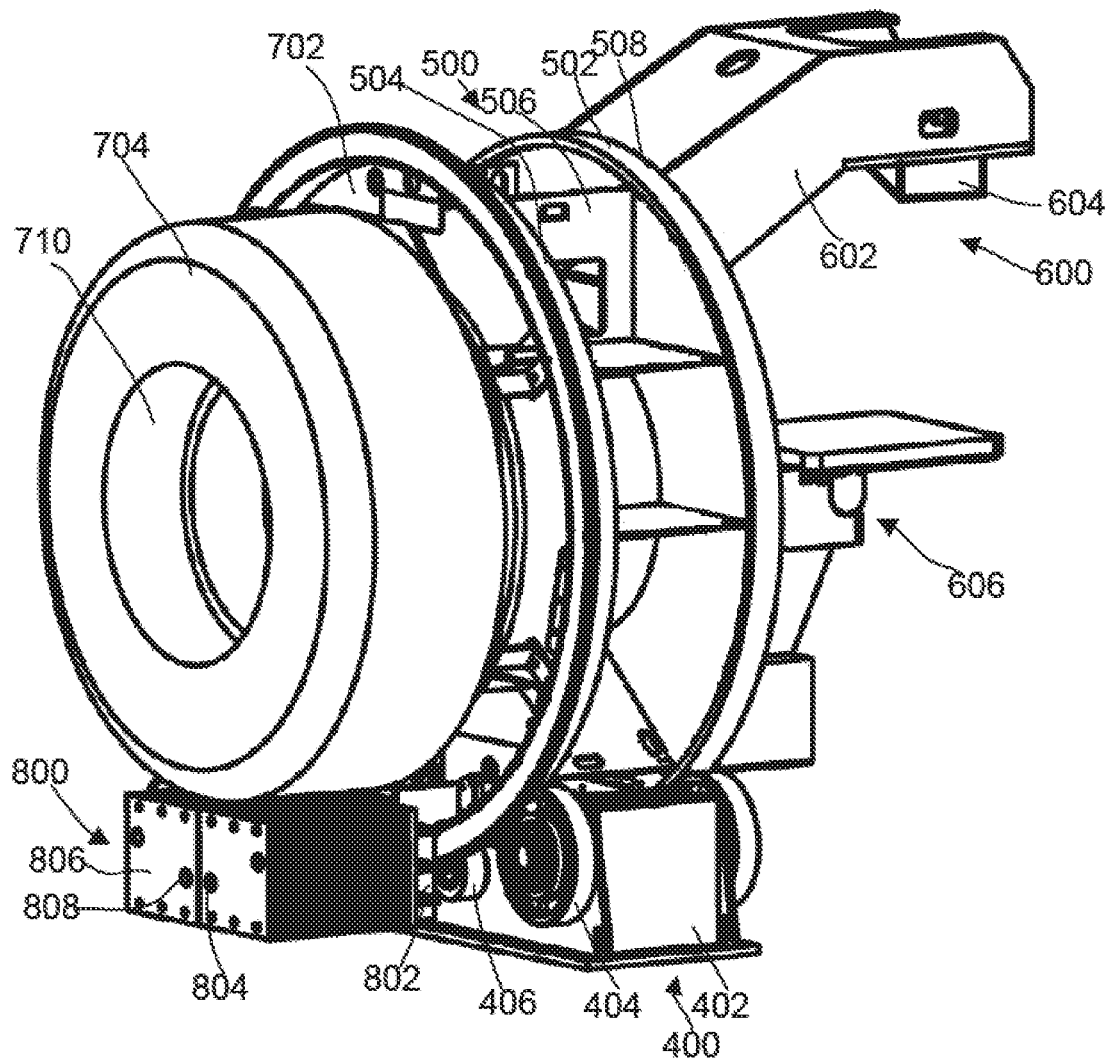
FIG. 3 is a schematic rear-side perspective view of a radiation therapy system according to some embodiments.
Figure 4:
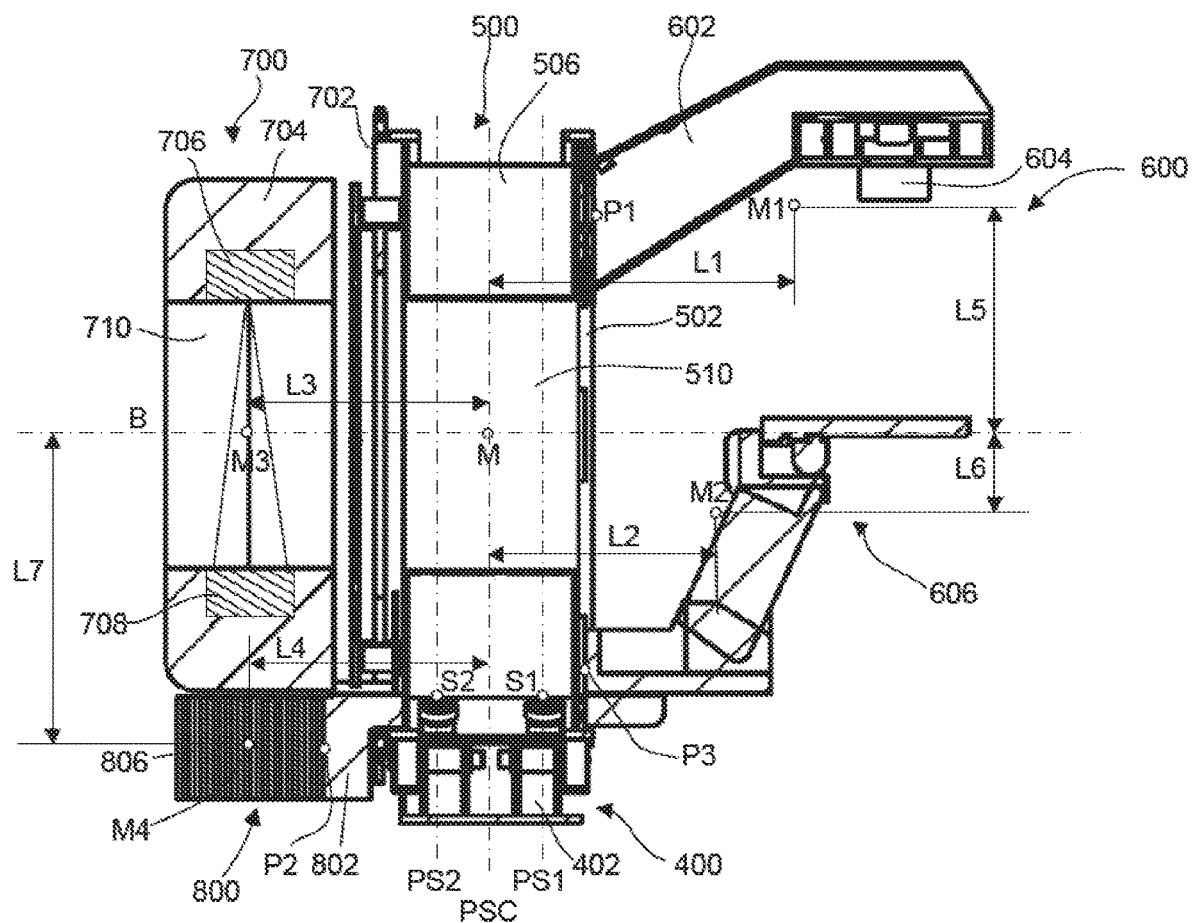
FIG. 4 schematically illustrates a cross-sectional view of a radiation therapy system according to some embodiments.
Figure 5:
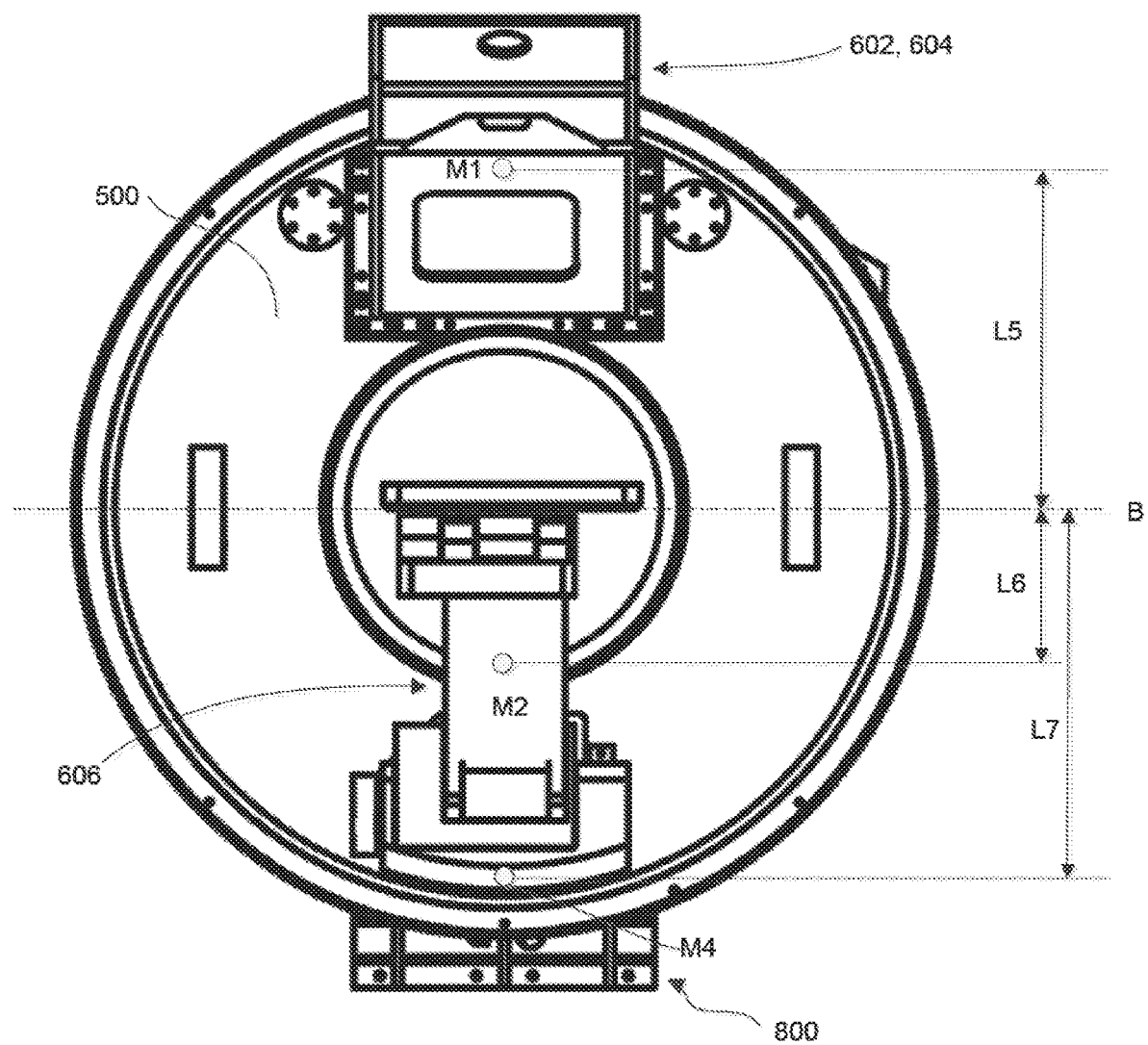
FIG. 5 schematically illustrates a front elevation of a radiation therapy system according to some embodiments.

FIGS. 1-5 illustrate a radiation therapy system 10 according to some embodiments. FIG. 1 schematically illustrates the radiation therapy system 10 including a housing 1000 and a couch assembly 900; FIG. 2 schematically illustrates the radiation therapy system 10 with the couch assembly 900 and without the housing 1000; FIG. 3 schematically illustrates the radiation therapy system 10 without the couch assembly 900 or the housing 1000; FIG. 4 schematically illustrates a cross-sectional view of FIG. 3; and FIG. 5 schematically illustrates a front elevational view of FIG. 3, wherein a base is removed.

Specifically, the radiation therapy medical apparatus 10 comprises a base 400, a gantry 500, a radiation therapy assembly 600, an imaging assembly 700, a counterbalance 800, a couch assembly 900 and a housing 1000. According to some embodiments, the housing 1000 encloses the gantry 500, a portion of the radiation therapy assembly 600, the imaging assembly 700 and the counterbalance 800.

The base 400 comprises a base body 402 horizontally supported on a support surface (i.e., a floor). Rollers 404, 406 are rotatably arranged on the base body 402, wherein the rollers 404 are arranged in a pair in the first horizontal direction along which the base 402 laterally extends, and the rollers 406 are arranged between the rollers 404 and also in a pair in the second horizontal direction along which the base 402 longitudinally extends. In addition, the base body 402 is provided with a driving motor (not shown) to drive one or more of rollers 404, 406.

Embodiments of the base 400 are not limited to those illustrated and described. For example, the rollers 406 could be removed, and the pair of rollers 404, 406 could be respectively replaced by one roller.

The gantry 500 is generally cylinder-shaped, which comprises a first cylindrical portion 502, a second cylindrical portion 504, and a plurality of connection portions 506 connecting the first cylindrical portion 502 to the second cylindrical portion 504. The connection portions 506 are rib-shaped, which may provide suitable rigidity to the gantry 500 while conserving weight. Outer rims 508 are respectively fixed to/formed from/extended from the first cylindrical portion 502 and the second cylindrical portion 504 along the axial direction. Cylindrical portions 502, 504 are respectively supported on the rollers 404, 406 by the outer rims 508, with the rollers 404, 406 being located on both sides of the base body 402.

Holes are defined in the cylindrical portions 502, 504, which in turn define the ends of a first through-hole 510 of the gantry 500. Typically, the rotation axis of the gantry 500 is the horizontal axial center of the first through-hole 510 when the gantry 500 is supported on the rollers 404, 406 of the base 400. According to some embodiments, the length of the first through-hole is between 400 and 800 mm or between 500 and 700 mm.

The structure of the gantry 500 according to some embodiments is not limited to that which is illustrated and described. For example, the size of the through-hole defined by the first cylindrical portion 502 could be different from the size of the through-hole defined by the second cylindrical portion 504. In another example, the gantry 500 comprises an annular frame and a cylinder, the inside of which is fixed to the annular frame. Alternatively, the gantry 500 may comprise a plurality of the fan-shaped portions or two semi-cylindrical portions which are fixed to each other by plurality of fasteners so as to omit the rib-shaped connection portions 506. The gantry 500 also may be peripherally supported on the base 400 in other ways, for example, via annular rails respectively extending from the inside of the first cylindrical portion 502 and the outside of the second cylindrical portion 504 along the axial direction. Moreover, the diameter of such annular rails may be more than, less than, or equal to the diameter of the gantry 500.

As previously recited, the base 400 could be provided with a driving motor. The output end of the driving motor may be connected to a driving sprocket gear. The outer rim 508 of the first cylindrical portion 502 or the second cylindrical portion 504 of the gantry 500 can be provided with sprocket teeth uniformly along the periphery, and as a result, the power of the driving motor can be transmitted to the gantry 500 via a chain respectively engaging the driving sprocket gear and the teeth to drive the gantry 500 to rotate about the horizontal axis. During rotation, the rollers 404, 406 can be rotated along with the gantry 500, so that the rollers 404, 406 function as supporting the gantry 500 on the one hand and reducing the friction upon the gantry 500 so as to increase rotation efficiency of the gantry 500. In some embodiments, the transmission between the power source (e.g., driving motor) on the base 400 and the gantry 500 may be replaced by other equivalent means such as a belt.

The radiation therapy assembly 600 comprises an arm 602, a radiation head 604, and a portal imaging unit 606. One end of the arm 602 is fixed to a first position P1 on a first side of the gantry 500, i.e., fixed to the first cylindrical portion 502, and the other end of the arm 602 extends outwardly. The radiation head 604 is fixed to this other end of the arm 602. The portal imaging unit 606 may comprise a support arm fixed to the gantry 500 and a portal imaging device connected to the support arm, wherein the portal imaging device is opposite to the radiation head 604 with respect to the central rotation axis during radiation therapy. Alternatively, the support arm is retractable, i.e., the support arm is driven by a dedicated motor to extend so that the portal imaging device is positioned opposite to the radiation head 604 so as to receive the beam from the radiation head 604 during radiation therapy, and the support arm may be retracted to a folded position in a non-imaging mode, if desired.

The structures, configurations and uses of the arm 602, the radiation head 604 and the portal imaging device 606 may comprise any which are or become known. Many patents, patent applications and/or other professional documents include detailed recitations with regard to the structure thereof, and thus will be not be repeated herein. Additionally, some embodiments omit the portal imaging unit. Portal imaging device 606 may also be substituted with a second imaging assembly arranged on the first side of the gantry 500. Such a second imaging assembly may differ from the aforementioned portal imaging device 606 in that the X-ray source of the second imaging assembly is independent from the radiation head 604.

The imaging assembly 700 is mounted on the second side of the gantry 500, i.e., mounted to the second cylindrical portion 504. Specifically, the imaging assembly 700 is a CT imaging assembly, which comprises a stator 702, a rotor 704, and imaging elements mounted on the rotor 704. More particularly, the stator 702 is fixed to the gantry 500, the rotor 704 is rotatably mounted to stator 702, and the imaging elements comprise at least an X-ray tube 706 and a detector 708 which are oppositely arranged with respect to the rotational center of the rotor 704.

In detail, referring to FIGS. 2 and 3, the stator 702 is fixed to the second cylindrical portion 504 such that the stator 702 may rotate along with rotation of the gantry 500. The stator 702 defines a central through-hole. The rotor 704 is connected to the stator 702 via a bearing such that the rotor 704 may rotate independently of the stator 702, and is electrically connected to the stator 702 via a slip ring so as to ensure power supply to the imaging elements on the rotor 704 when the rotor 704 is rotated with respect to the stator 702.

The rotor 704 also defines a center through-hole in which an object to be imaged may be placed, such as a human body. Center through-holes of the stator 702 and the rotor 704 constitute a second through-hole 710 which may be generally coaxial with the first through-hole 510.

According to the embodiments of FIGS. 1-5, the stator 702 of the CT imaging assembly 700 is adjacent to the second side of the gantry 500, and the rotor 704 is rotatably mounted to the stator 702 via a bearing. That is, the rotor 704 is positioned further away from the gantry 500 than the stator 702. However, alternatively, the rotor 704 equipped with imaging elements could be rotatably mounted to the stator 702 via a bearing, followed by securing the stator 702 to the second side of the gantry 500 via fastening means along the mounting direction in which the rotor 704 is adjacent to the second side of the gantry 500. Consequently, the stator 702 would be further away from the second side of the gantry 500 than the rotor 704 would be from the second side of the gantry 500. Such an arrangement would reduce the distance between the imaging plane of the imaging assembly 700 and the isocenter of the radiation therapy assembly 600 in comparison to the configuration of FIGS. 1-5, assuming other component sizes and connections are identical.

The imaging assembly 700 may also be an MR imaging assembly or a positron emission tomography (PET) imaging assembly, allowing omission of the rotor 704. For example, if the imaging assembly 700 is an MR imaging assembly, the magnetic resonance imaging elements such as a main magnet, gradient coils, and pulse coils can be arranged within the stator 702. If the imaging assembly 700 is a PET imaging assembly, the detector ring can be directly arranged to the stator 702.

The above-described imaging assembly 700 may be considered a counterbalance for balancing the radiation therapy assembly 600, which will be described in detail hereinafter.

The counterbalance 800 comprises a bracket 802 fixed to the second cylindrical portion 504, a rod 804 extending outwardly from the bracket 802, and a plurality of weight plates 806. Each of the weight plates 806 defines through-hole 808 so that the weight plates 806 can be suspended on the rod 804 and detachably fixed to the gantry 500 via fasteners such as bolts. It could be understood by one of skilled in the art that, the weight of the counterbalance 800 is adjustable, for example, it is adjustable via adding or removing the weight plates 806. Alternatively, the counterbalance 800 as a whole could be fixed to the gantry in a fixed manner or could include at least one portion integral with the gantry. In another alternative embodiment, the counterbalance could comprise a weight fixed to the gantry or extending from the gantry, and another adjustable weight supported on the gantry.

Referring to FIGS. 3-5, a technical solution will now be described with reference to counterbalance 800. According to some embodiments, the connection between the gantry 500 and the base 400 is characterized in that the gantry 500 presses on the rollers 404, 406 on the base 400 via the outer periphery 508, i.e., the gantry 500 is "placed on" or "supported on" but not "fixed to" the base 400. Since the arm 602 and the radiation head 604 secured to one side of the gantry 500 are cumbersome, and considering the rotational balance of the whole apparatus, the resulting force moment may cause the gantry 500 to be susceptible to dislodging, e.g., tipping, from the base 400. Thus, according to some embodiments, one or more counterbalances are arranged so as to prevent the gantry 500 from dislodging from the base 400 and also to ensure balance of the gantry 500 during rotation.

According to some embodiments, a counterbalance may be arranged as follows. The imaging assembly 700 serves as a first counterbalance for balancing the radiation therapy assembly 600. The counterbalance 800 is configured to cooperate with the imaging assembly 700 for preventing the gantry 500 from turnover under the action of the radiation therapy assembly 600 and for dynamically balancing the radiation therapy assembly 600 with respect to the rotation axis of the gantry 500.

Specifically, as a first counterbalance, the imaging assembly 700 is mounted generally coaxially to the second side of the gantry 500. The counterbalance 800 is fixed to the second side of the gantry 500, and generally offset from the arm 602 (or the radiation head 604) with respect to the rotation axis. With respect to FIG. 4, the counterbalance 800 is secured to the second position P2 on the second side of the gantry 500, wherein the second position P2 is opposite to the first position P1 of the arm 602 with respect to the rotation axis B. Further, the center of the second position P2 generally falls on a line which is parallel to the line connecting the rotation center of the radial rotation plane of the first side of the gantry 500 and the first position P1 and passing through the rotation center of the radial rotation plane of the second side of the gantry 500. As shown in the Figures, the second position P2 is generally peripherally offset from the first position P1 by 180 degrees.

According to some embodiments, the angular orientation of the second position P2 of the counterbalance 800 is generally the same as the position P3 of the portal imaging device (i.e., the angle by which P2 is offset from a vertical line in the same plane is generally the same as the angle by which P3 is offset from a vertical line in the same plane). In other words, the position for mounting the counterbalance 800 to the gantry 500 is generally symmetrical with the position for mounting the portal imaging device 606 to the gantry 500 with respect to the central rotation plane of the gantry 500.

In order to configure the counterbalance 800 to cooperate with the imaging assembly 700 to inhibit the gantry 500 from tipping over under the action of the radiation therapy assembly 600, the counterbalance 800, the imaging assembly 700, the gantry 500, and the radiation therapy assembly 600 may be configured such that the mass center M project between the points S1 and S2 of the base 400 supporting the gantry 500, i.e., the mass center M is located in the plane PSC between the vertical planes PS1, PS2, as shown in FIG. 4.

It may be assumed in some embodiments that the mass distribution of the imaging assembly 700 with respect to the horizontal rotation axis is generally even, that is, the imaging assembly 700 is self-balanced during rotation.

More specifically, referring to FIG. 4, if the distance between the mass center M1 of the arm 602 and the radiation head 604 and the plane PSC of the mass center M is about L1, and the distance between the mass center M2 of the portal imaging unit 606 of the radiation therapy assembly 600 and the plane PSC of the mass center M is about L2, the distance between the mass center M3 of the imaging assembly 700 and the plane PSC of the mass center M is about L3, and the distance between the mass center M4 of the counterbalance 800 and the plane PSC of the mass center M is about L4, some embodiments are configured to conform to the following formula in order to inhibit the gantry 500 from dislodging from the base 400:

$$M1 \times L1 + M2 \times L2 = M3 \times L3 + M4 \times L4$$

It should be understood that, due to requirements for assembly, some other components may be mounted on the gantry, and therefore the above formula may need to be changed correspondingly.

Referring to FIG. 5, if the distance between the mass center M1 of the arm 602 and the radiation head 604 of the radiation therapy assembly 600 and the rotation axis B is about L5, and the distance between the mass center M2 of the portal imaging unit 606 and the rotation axis B is about L6, and the distance between the mass center M4 of the counterbalance 800 and the rotation axis B is about L7, some embodiments are configured to conform to the following formula so as to provide balance during rotation:

$$M1 \times L5 = M2 \times L6 + M4 \times L7$$

According to some embodiments, the summed mass of the arm 602 and the radiation head 604 is between 1200 kg and 1300 kg, the mass of the portal imaging unit 606 is between 200 kg and 300 kg, and the mass of each of the imaging assembly 700 and the counterbalance is about 1000 kg.

It should be understood that, the mass of the counterbalance may be calculated so as to achieve balance in clockwise and counterclockwise rotational directions according to above principles.

In the above-mentioned embodiments, the imaging assembly 700 comprises the stator 702 and the rotor 704. However, in other embodiments, the imaging assembly 700 could also include a rotor, wherein the specific imaging elements (i.e., in the case of the CT imaging assembly, an X-ray tube and a detector) are arranged on the rotor; and in other embodiments, the imaging assembly 700, such as an MR imaging assembly, may only include a stator, on which the specific imaging elements such as a main magnet, gradient coils, and pulse coils can be arranged.

The counterbalance 800 can be wholly/partially detachably secured to the gantry 500, or wholly/partially secured to the gantry 500 in a non-detachable manner, or wholly/partially extended from and integral with the gantry 500 itself. The counterbalance 800 can be located at a proper position according to the above-mentioned method. It also should be understood that the weight of the counterbalance 800 may be adjustable, for example, via adding or removing weight plates; and alternatively, the counterbalance 800 also can be wholly or partially moved along the radial direction or axial direction inwardly and/or outwardly so as to adjust the location of the mass center M.

Alternatively, the radiation therapy assembly 600 may include another counterbalance generally adjacent to the portal imaging device 606 and opposite to the arm 602 and/or the radiation head 604 with respect to the rotation axis.

A radiation therapy medical apparatus according to FIGS. 1-5 and/or some embodiments may be suitably compact. Specifically, the distance between the isocenter (i.e., the intersection point of the longitudinal axis of the radiation beam and the rotation axis of the gantry 500) of the radiation therapy assembly 600 and the imaging plane of the imaging assembly 700 may be between 1300-2300 mm, 1300-2000 mm, or 1300-1700 mm.

A radiation therapy medical apparatus 10 according to some embodiments in comparison to conventional systems, exhibits a smaller distance between the imaging plane of the imaging assembly 700 and the isocenter of the radiation therapy assembly 600. This technical solution is achieved at least in part by mounting the imaging assembly 700 to the gantry 500 while arranging the counterbalance 800 as described herein. More particularly, the common gantry 500 of the radiation therapy assembly 600 and the imaging assembly 700 results in reducing the entire occupied volume and the length in the first horizontal direction, and, by configuring the imaging assembly 700 as a first counterbalance and configuring the counterbalance 800, dynamic balance may be simultaneously achieved.

Figure 6:
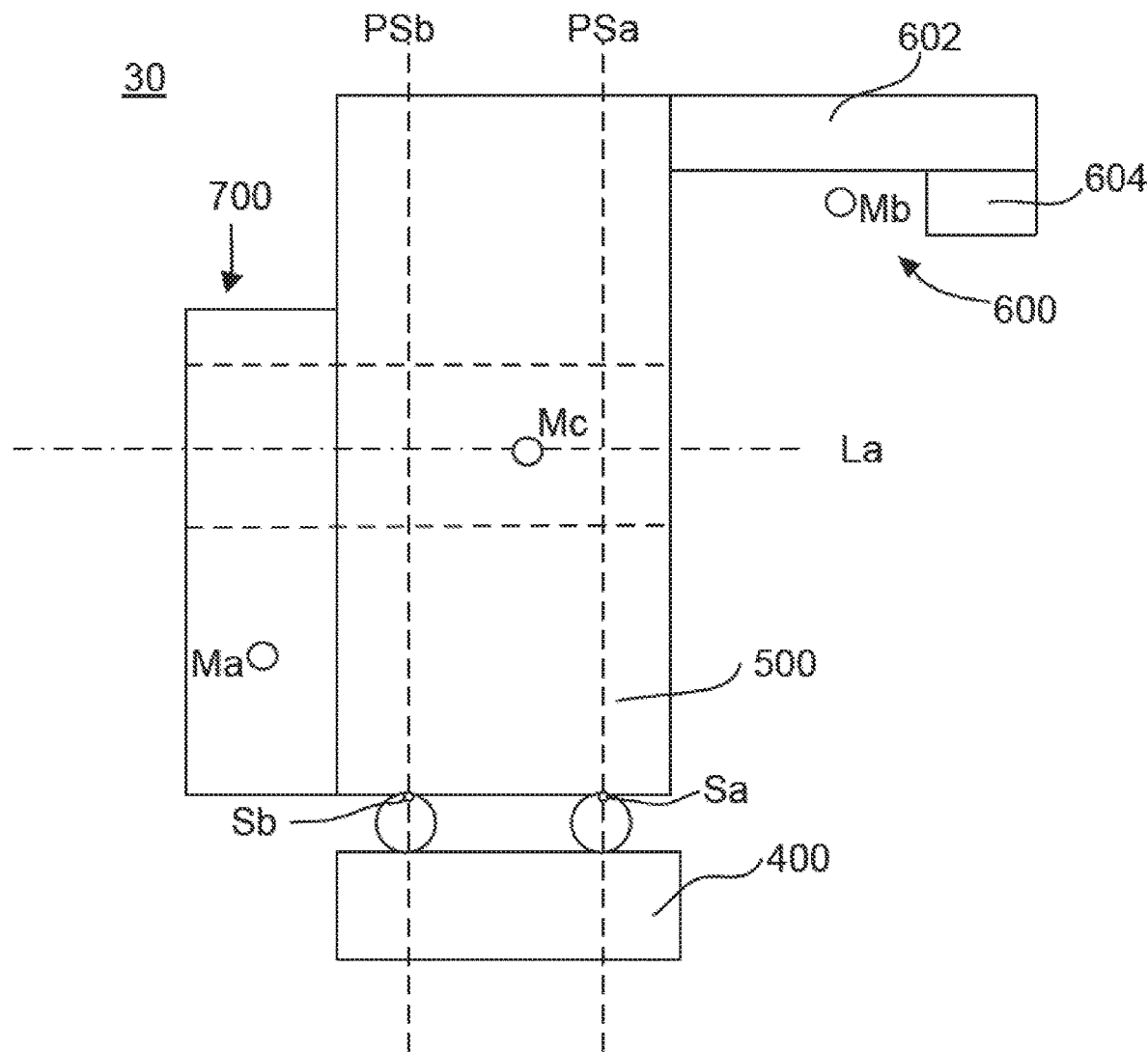
FIG. 6 is a schematic diagram of a radiation therapy system according to some embodiments.

A radiation therapy medical apparatus 30 according to some embodiments is schematically illustrated in FIG. 6. The medical apparatus 30 comprises a base 400, a gantry 500, a radiation therapy assembly 600 and an imaging assembly 700. Specifically, the gantry 500 is peripherally and rotatably supported on the base 400. The radiation therapy assembly 600 at least comprises an arm 602 and a radiation head 604. In some embodiments, the radiation therapy assembly 600 further comprises a portal imaging device. One end of the arm 602 is secured to the first position on the first side of the gantry 500 and other end thereof extends outwardly. The radiation head 604 is secured to the other end of the arm 602.

The imaging assembly 700 is mounted to the second side of the gantry 500, and configured as a counterbalance to the radiation therapy assembly 600. The imaging assembly 700 is configured such that mass center Ma thereof is offset away from the mass center Mb of the radiation therapy assembly 600 with respect to the rotation axis La of the gantry 500. The imaging assembly 700 is configured such that the projection of the mass center Mc of the imaging assembly 700, the gantry 500, and the radiation therapy assembly 600 on a horizontal plane falls between the support points Sa and Sb of the base 400 supporting the gantry 500. More specifically, the mass center Mc is located between the vertical planes PSa and PSb.

The imaging assembly 700 comprises a stator, or a rotor, or a combination of a stator and a rotor, and further comprises imaging elements. Correspondingly, the imaging elements are arranged on the stator, on the rotor, or on the combination of the stator and the rotor. The imaging elements could comprise an X-ray tube and a detector if the imaging assembly is a CT imaging assembly, and a main magnet, gradient coils, and pulse coils if an MR imaging assembly.

The radiation therapy medical apparatus 30 is configured to resist tipping by means of a counterbalance, and differs from the above-mentioned radiation therapy apparatuses 10, 20 in that the counterbalance 800 is not present and the imaging assembly 700 serves as the counterbalance. In this apparatus 30, the mass center of the imaging assembly 700 is offset away from the mass center of the radiation therapy assembly 600 with respect to the rotation axis of the gantry 500.

Figure 7:
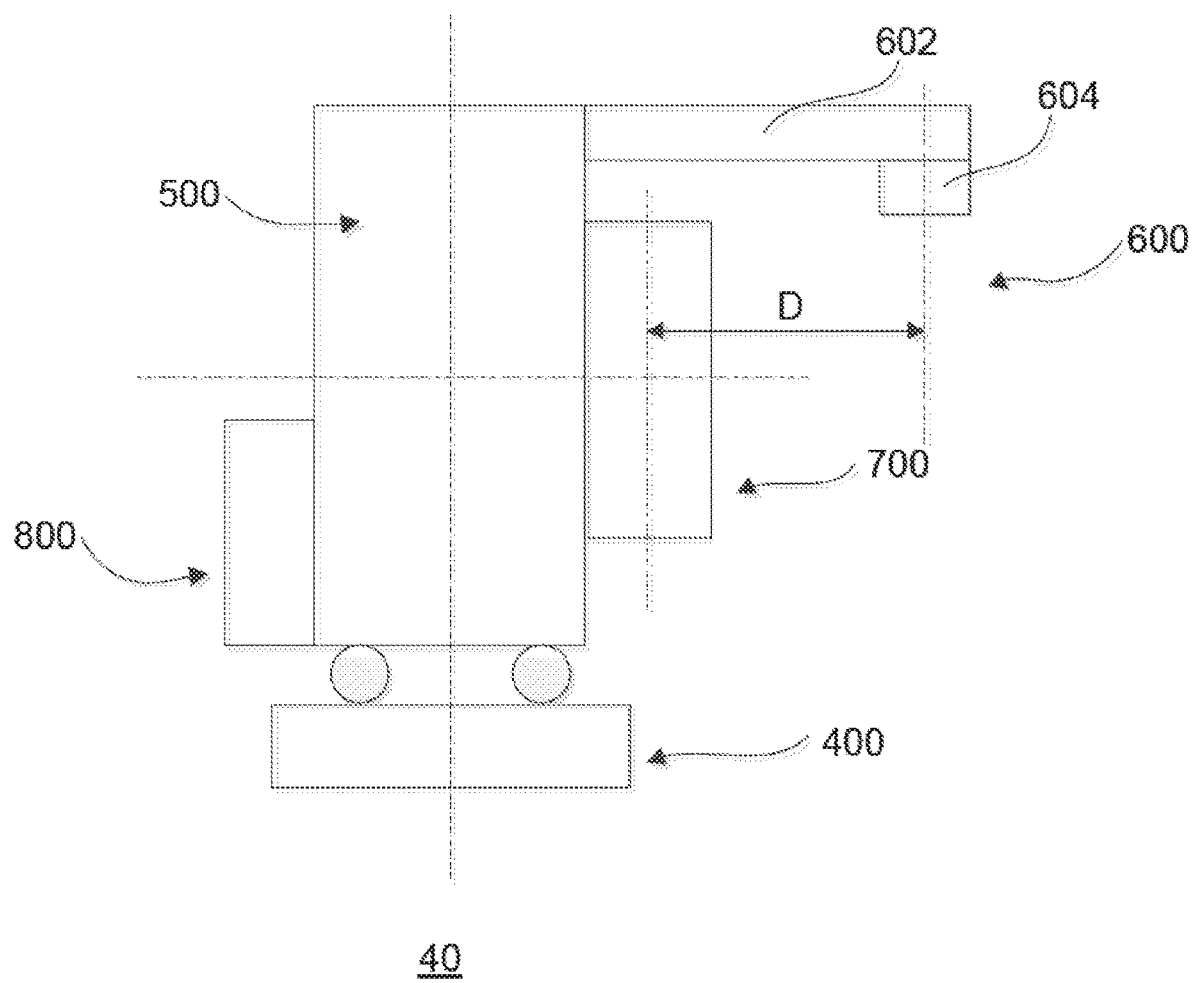
FIG. 7 is a schematic diagram of a radiation therapy system according to some embodiments.

FIG. 7 shows a radiation therapy medical apparatus 40 according to some embodiments. The radiation therapy medical apparatus 40 comprises: a base 400; a cylindrical gantry 500 peripherally and rotatably supported by the base 400; a radiation therapy assembly 600, comprising an arm 602 and a radiation head 604, wherein one end of the arm 602 is fixed to a first side of the gantry 500 and the other end to which the radiation head 604 is fixed extends outwardly; an imaging assembly 700 mounted to the first side of the gantry 500; and a counterbalance 800, fixed to the second side of the gantry 500, and configured such that the center of mass of the counterbalance 800, the gantry 500, the radiation therapy assembly 600, and the imaging assembly 700 falls between the supporting planes of the base 400 supporting the gantry 500 to resist tipping, and further configured such that the gantry 500 is rotatable in a dynamic balanced state.

The distance D between the imaging plane of the imaging assembly 700 and the isocenter of the radiation therapy assembly 600 may be between 500 mm and 1600 mm. The radiation therapy medical apparatus 40 may further comprise a couch assembly comprising a couch plate. The movable distance for said couch plate from a first position where the patient is imaged by the imaging assembly 700 to a second position where the patient is radiated by the radiation therapy assembly 600 may be between 1100 mm and 3600 mm, or 1100 mm and 2500 mm, or 1100 mm and 2200 mm. The distance range 1100 mm to 3600 mm is adapted for a whole-length scan mode, and other distance ranges are adapted for a predetermined scan range mode.

In this embodiment, the imaging assembly 700 may be a CT imaging assembly, an MR imaging assembly, or a PET imaging assembly. Moreover, the imaging assembly 700 is substantially coaxial with the gantry 500. The counterbalance 800 is oppositely offset from the radiation head 604 with respect to the rotation axis of the gantry 500. Alternatively, the weight of the counterbalance 800 can be adjustable.

Figure 8:
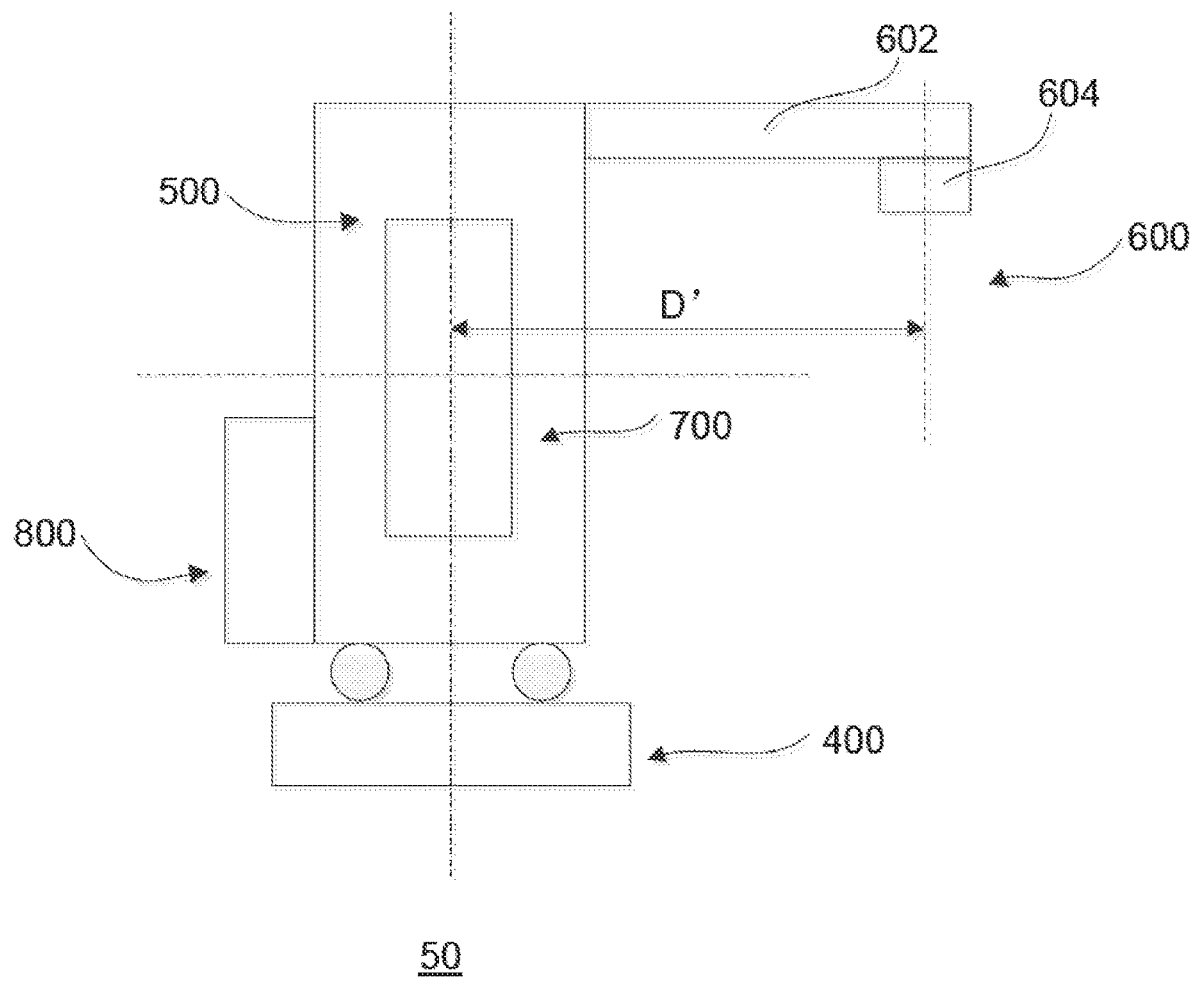
FIG. 8 is a schematic diagram of a radiation therapy system according to some embodiments.

As shown in FIG. 8, a radiation therapy medical apparatus 50 is disclosed according to another embodiment, which differs from the medical apparatus 40 in that the imaging assembly 700 is arranged within the gantry 500. According to some embodiment, the imaging assembly 700 also can be partially arranged within the gantry 500.

The distance D' from the imaging plane of the imaging assembly 700 to the isocenter of the radiation therapy assembly 600 may be between 800 mm and 2000 mm. The movable distance of the patient support from the first position at which a patient is imaged by the imaging assembly 700 to the second position at which the patient is radiated by the radiation therapy assembly 600 may be between 1400 mm and 4000 mm, 1400 mm and 2900 mm, or between 1400 mm and 2600 mm, wherein the distance range 1400 mm to 4000 mm is adapted for a whole-length scan mode, and the other distance ranges are adapted for a predetermined scan range mode.

The imaging assembly 700 may be a CT imaging assembly, an MR imaging assembly, or a PET imaging assembly, and moreover, the imaging assembly 700 is substantially coaxial with the gantry 500. The counterbalance 800 is oppositely offset from the radiation head 604 with respect to the rotation axis of the gantry 500 in order to increase the resistance of apparatus 40 to tipping. The weight of the counterbalance 800 may be adjustable.

Figure 9:
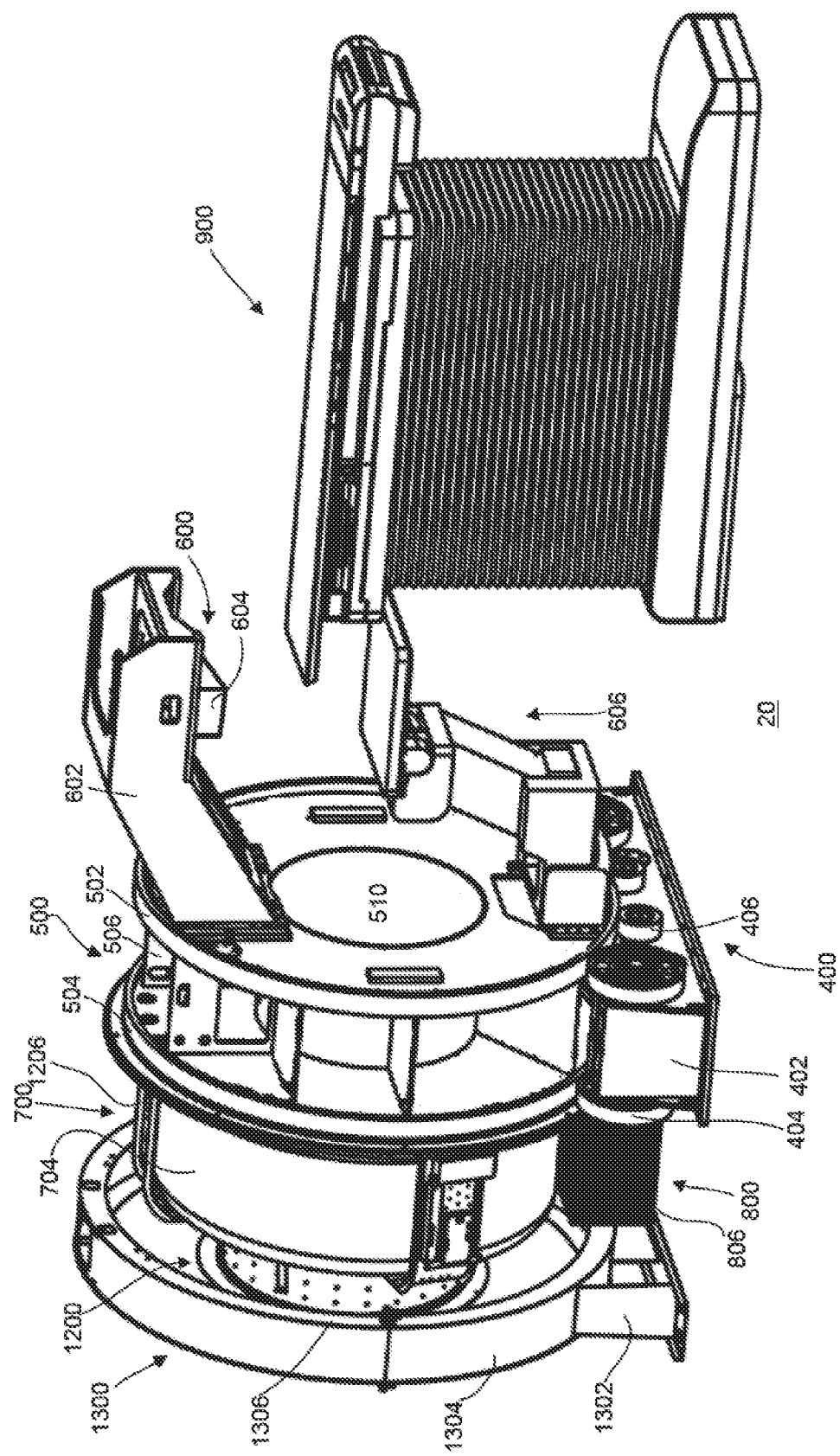
FIG. 9 schematically illustrates a front-side perspective view of a radiation therapy system according to some embodiments.
Figure 10:
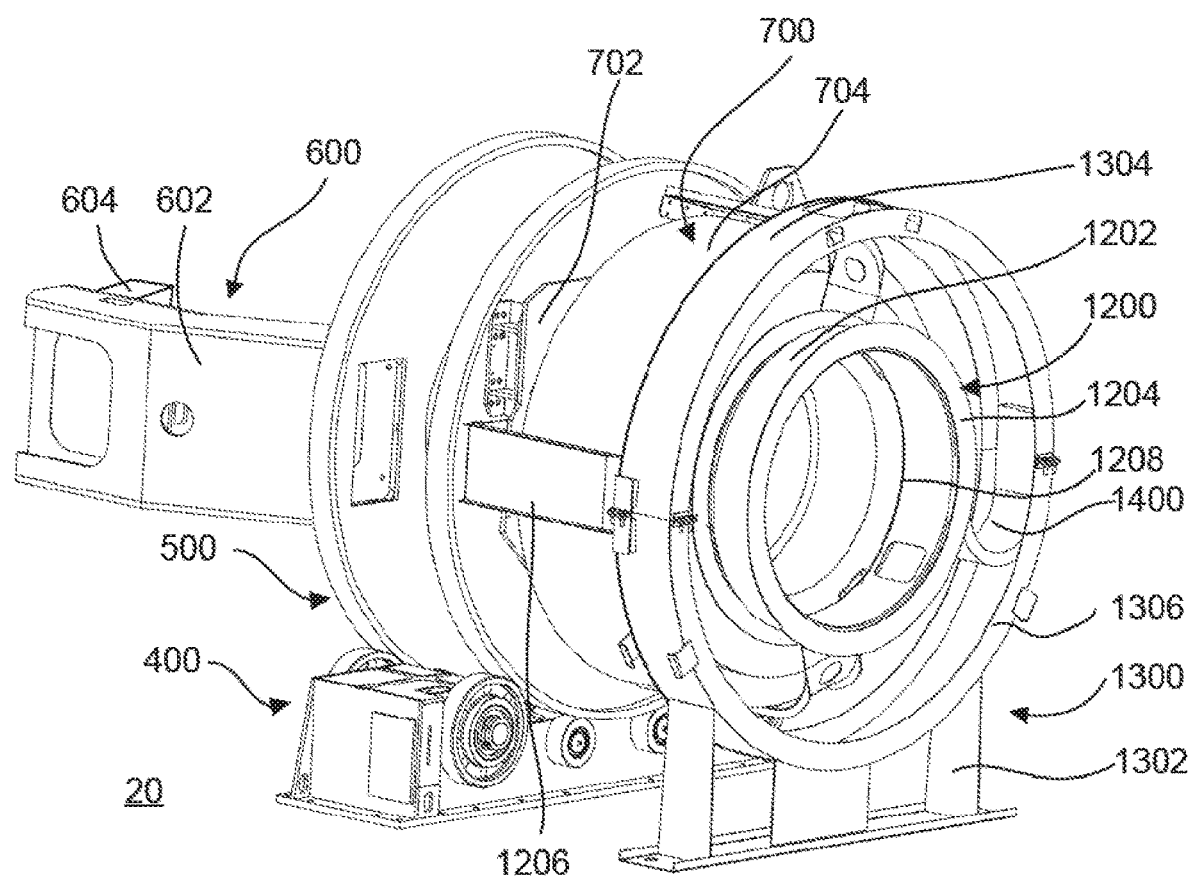
FIG. 10 schematically illustrates a rear-side perspective view of a radiation therapy system according to some embodiments.
Figure 11:
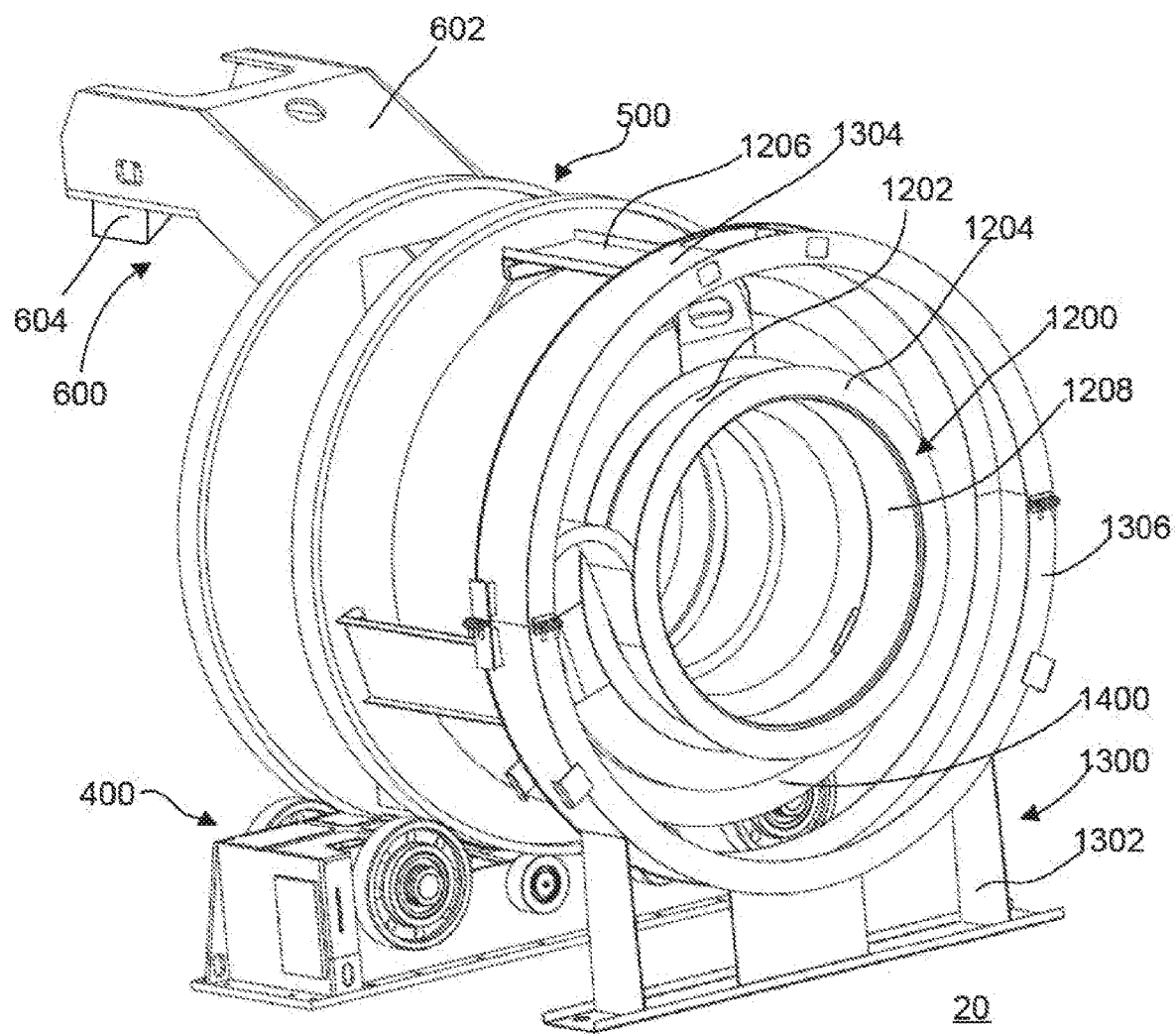
FIG. 11 schematically illustrates a rear-side perspective view of a radiation therapy system according to some embodiments.

FIGS. 9-11 illustrate a radiation therapy medical apparatus 20. The radiation therapy medical apparatus 20 is similar to the above-described radiation therapy medical apparatus 10, and further comprises a cylinder 1200, a drag chain carrier 1300 and a drag chain (also known as a cable carrier, or a cable track) 1400.

Specifically, the cylinder 1200 is fixed to the second side of the gantry 500 adjacent to the imaging assembly 700. The drag chain carrier 1300 comprises a cylindrical carrier body 1304 concentrically surrounding the cylinder 1200 and defining, with the cylinder 1200, an annular track. The drag chain 1400 is arranged within the annular track, and one end of the drag chain 1400 is fixed to the cylinder 1200 while the other end is fixed to the cylindrical carrier body 1304. One or more electrical and/or signal cables may be carried by the drag chain 1400, ends of which are electrically connected to the radiation therapy assembly 600 and/or the imaging assembly 700 and other ends of which are electrically connected to power sources or other devices exterior to the apparatus 20.

More specifically, the cylinder 1200 is fixed to the second side of the gantry 500 via a plurality of beams 1206 peripherally and uniformly arranged, and the cylinder 1200 and the gantry 500 are generally coaxial. Edges of the cylindrical body 1202 of the cylinder 1200 on both sides extend outwardly along the radial direction to form rims 1204 which constitute an outer rail together with the cylindrical body 1202. In the axial direction of the gantry 500, the cylinder 1200 defines a third through-hole 1208 which is in communication with and may be substantially co-axial with the first through-hole 510 and the second through-hole 710. By virtue of this arrangement, the cylinder 1200 does not interfere when the patient support 908 enters into the first through-hole 510 and the second through-hole 710 to acquire an image of a patient.

The drag chain carrier 1300 comprises a drag chain carrier base 1302 for supporting the drag chain carrier body 1304 thereon. More specifically, the drag chain carrier base 1302 is supported by the floor, and the drag chain carrier body 1304 is generally cylindrical and the edges thereof extend inwardly along the radial direction to form rims 1306. As a result, the drag chain carrier 1304 forms an inner rail. Moreover, as shown, the drag chain carrier base 1302 is arranged such that the drag chain carrier body 1304 is radially arranged outside of the cylinder 1200 and generally coaxial with the cylinder 1200. The inner rail of the drag chain carrier body 1304 and the outer rail of the cylinder 1200 face one another in the radial direction and are spaced to form the aforementioned annular track. The above-mentioned drag chain 1400, which could be a bidirectional curve drag chain, is arranged in the annular track.

During assembly, a cable connected to an external power source (e.g., a floor-located power outlet) could wind around the outer surface of the drag chain carrier body 1304, enter into the inner surface of the drag chain carrier body 1304 via a hole defined by the drag chain carrier body 1304 and positioned at the area at which the drag chain carrier body 1304 is connected to the drag chain 1400, further pass through the drag chain 1400 to be carried thereby, and out of the connection area of the drag chain 1400 and the cylinder 1200 to various electronic components of the radiation therapy assembly 600 and/or the imaging assembly 700 along the beams 1206 between the cylinder 1200 and the gantry 500. The cable could be fixed or fastened or bound to each component around which the cable winds via holes defined by the components and by cable-bunchers, such as flexible cable-fasteners.

Implementations of the foregoing arrangement of the cylinder 1200, the drag chain carrier 1300 and the drag chain 1400, may allow transfer of electricity from a power source to the radiation therapy assembly 600 and/or the imaging assembly 700, while protecting the cables from damage. In a case that the imaging assembly 700 is a CT imaging assembly, electricity could be transferred by the slip ring between the stator and the rotor.

The required length of the drag chain 1400 in the annular track may be determined by the rotation range of the gantry 500 on the base 400. According to some embodiments, it is preferable that the length of the drag chain 1400 is predetermined to allow the gantry 500 to rotate within −180 to +365 degrees, in order to fully consider the rotation range of the arm 602 and the radiation head 604 of the radiation therapy assembly 600, safety, and other factors.

The drag chain 1400 may support power cables, signal cables and/or cooling medium tubes. The cylinder 1200, the drag chain carrier 1300 and the drag chain 1400 are not limited to use with a radiation therapy medical apparatus as shown in FIGS. 9-11. For example, embodiments may be used in conjunction with a medical apparatus without the imaging assembly of the radiation therapy medical apparatus 20, or with a medical apparatus arranging the imaging assembly of the radiation therapy apparatus 20 on the same side as the radiation therapy assembly, or with a medical apparatus arranging the imaging assembly at least partially inside of the.

Figure 12:
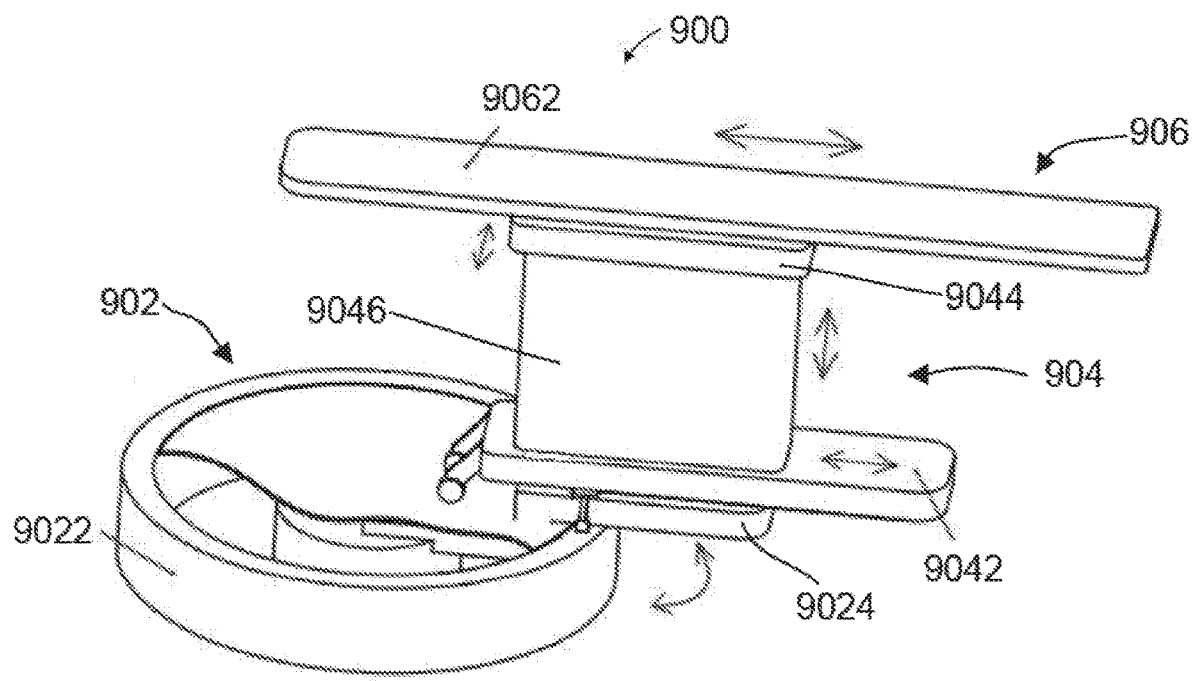
FIG. 12 is a rear-side perspective view of a couch assembly according to some embodiments.

As shown in FIG. 12, the couch assembly 900 comprises a first support assembly 902, a second support assembly 904, a third support assembly 906 and a patient support 908 (as shown in FIG. 1). Specifically, the first support assembly 902 comprises a base 9022 and a first support plate 9024, wherein the base 9022 includes a cylindrical periphery serving as an annular track for supporting the first support plate 9024 thereon. The second support assembly 904 comprises a second support plate 9042, a third support plate 9044, and a height adjustment mechanism 9046 secured between the second support plate 9042 and the third support plate 9044. The height adjustment mechanism 9046 may comprise a shears-like adjustment mechanism, for example, through which a height of the third support plate 9044 may be adjusted. A sliding mechanism may be arranged between the second support plate 9042 and the first support plate 9024 such that the second support plate 9042 is slidable in a first horizontal direction with respect to the first support plate 9024. For example, two parallel grooves can be defined in the second support plate 9042 and two corresponding parallel guiderails can be arranged on the first support plate 9024. Alternatively, two parallel guiderails can be arranged on the second support plate 9042, and correspondingly, two parallel grooves can be defined in the first support plate 9024.

The third support assembly 906 comprises a fourth support plate 9062. Specifically, structures engaging each other can be arranged between the fourth support plate 9062 and the third support plate 9044. For example, two parallel grooves can be defined in the fourth support plate 9062, and correspondingly, two parallel guiderails can be arranged on the third support plate 9044. Alternatively, two parallel guiderails can be arranged on the fourth support plate 9062, and two corresponding parallel grooves can be defined in the third support plate 9044. Accordingly, the fourth support plate 9062 can slide in a second horizontal direction with respect to the third support plate 9044.

The upper surface of the fourth support plate 9062 defines an opening facing upward and extending along a first horizontal direction, in which a slidable plate (not shown) can be arranged. The patient support 908 of FIG. 1 is secured to the slidable plate and can slide in the first horizontal direction along with the slidable plate. Dedicated and independently-controllable mechanisms may be used to drive rotation of the first support plate 9024 with respect to the base 9022, sliding of the second support plate 9042 in the first horizontal direction with respect to the first support plate 9024, height adjustment of the height adjustment mechanism 9046, sliding of the fourth support plate 9062 in the second horizontal direction with respect the third support plate 9044, and sliding of the slidable plate on the fourth support plate 9062 in the first horizontal direction with respect to the fourth support plate. Alternatively, rotation of the first support plate 9024 with respect to the base 9022, sliding of the second support plate 9042 in the first horizontal direction with respect to the first support plate 9024, and height adjustment of the height adjustment mechanism 9046 may be driven by dedicated mechanisms, and other movements can be adjusted manually and locked by locking mechanisms.

During assembly, the base 9022 can be mounted under the floor of a treatment room or an imaging room. Additionally, the rotatable angle range of the first support plate 9024 with respect to the base 9022 can be 0 to 180 degrees. Other assembly arrangements can be adopted, and the rotatable angle range of the first support plate 9024 with respect to the base 9022 also can be more than 180 degrees or less than 180 degrees.

According to some embodiments, the couch assembly 900 can rotate about the vertical axis of the base 9022, can move along the first horizontal direction, can move along the second horizontal direction, can move along the vertical direction, and also can perform any combination of these motions. Specifically, since the movement range of the patient support 908 of the couch assembly 900 in the first horizontal direction depends on the movable distance of the second support plate 9042 with respect to the first support plate 9024 and the movable distance of the slidable plate supporting the patient support 908 in the first horizontal direction with respect to the fourth support plate 9062, the movement range of the patient support 908 in the first horizontal direction is the larger distance. As shown in FIG. 12, in order to achieve better rigidity and reliability for the entire structure, the movable length of the second support plate 9042 in the first horizontal direction with respect to the first support plate 9024 may be less than the movable length of the slidable plate (or the patient support 908) in the first horizontal direction with respect to the fourth support plate 9062. This arrangement considers the flexible deformation of the first support plate 9024 caused by the total weight of the second support assembly 904, the third support assembly 906 and the patient on the patient support 908.

Figure 13:
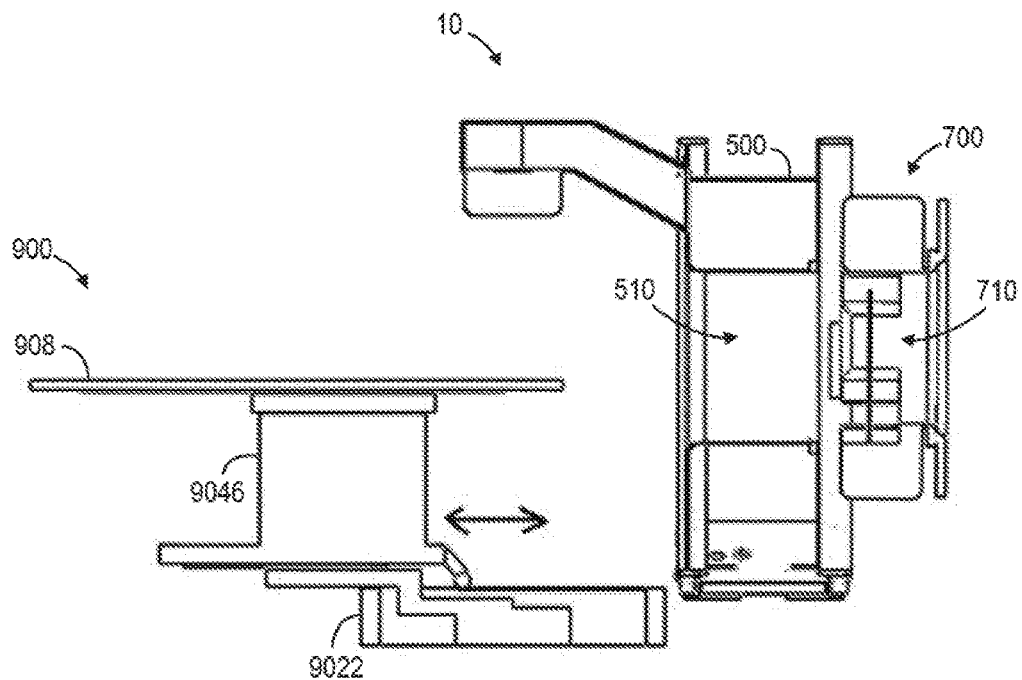
FIG. 13 is a side cross-sectional view of a system according to some embodiments.

The above-described couch assembly 900 may be used in conjunction with the radiation therapy medical apparatuses 10, 20 described herein. More specifically, during imaging by the imaging assembly 700 such as a CT imaging assembly, the first support plate 9024 of the couch assembly 900 could first be rotated from a position as shown in FIG. 13 to a position immediately adjacent to the gantry 500 such that the first horizontal direction is parallel to the rotation axis of the gantry 500. Next, the second support plate 9042 could be moved to a position immediately adjacent to the gantry 500 with respect to the first support plate 9024 in the first horizontal direction, and the height adjustment mechanism 9046 could be subsequently adjusted such that the patient is at a certain height. The patient support 908 fixed on the slidable plate is then moved toward the gantry 500 in the first horizontal direction with respect to the fourth support plate 9062 to the imaging plane of the imaging assembly 700 so as to finish a scan of the predetermined scan area.

Figure 14:
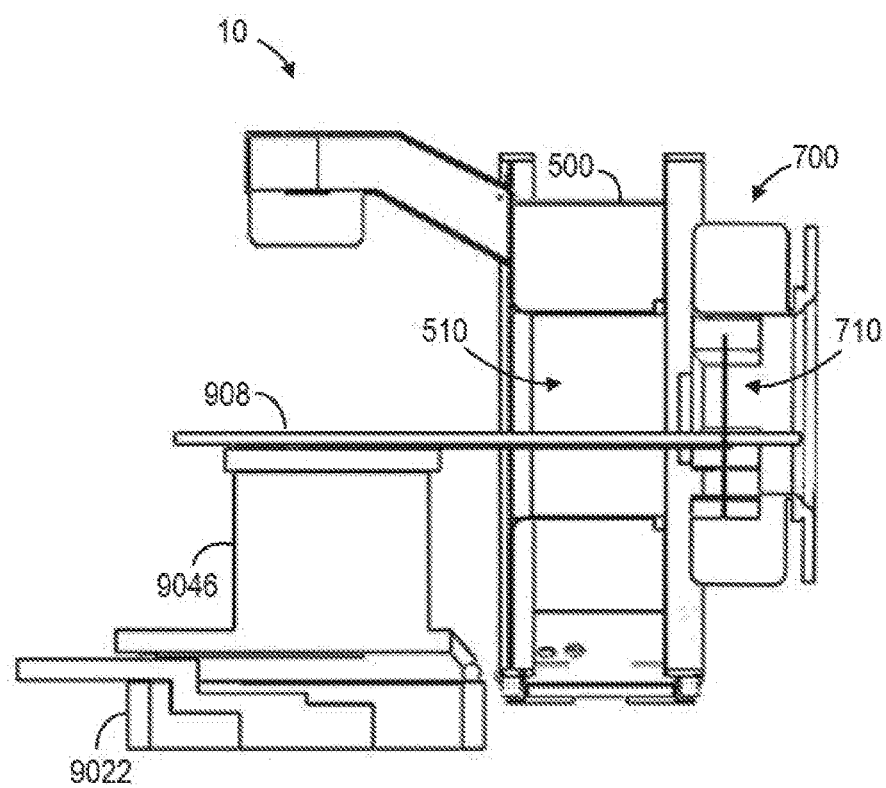
FIG. 14 is a side cross-sectional view of a system according to some embodiments.
Figure 15:
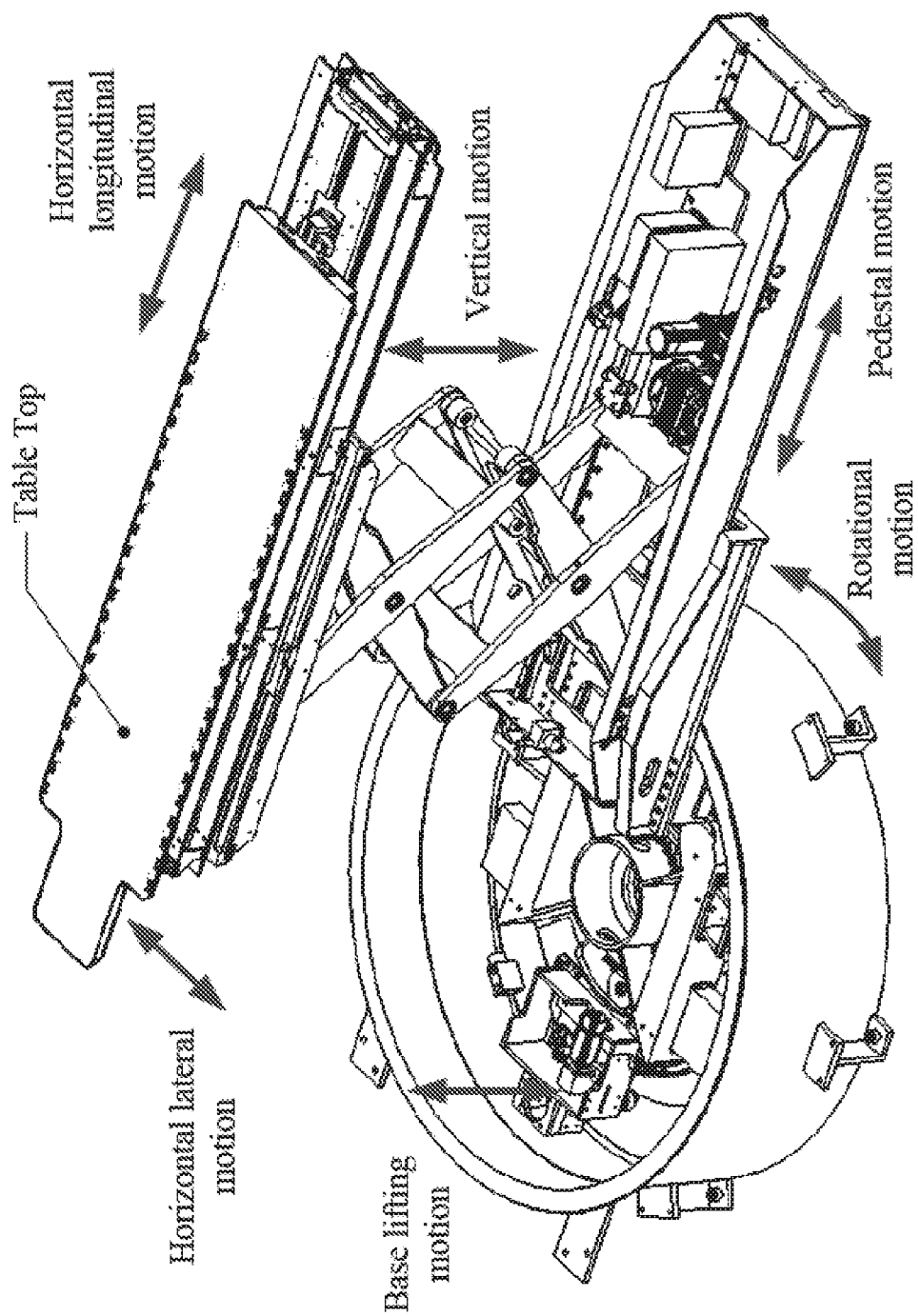
FIG. 15 is a rear-side perspective view of a couch assembly according to some embodiments.
Figure 16:
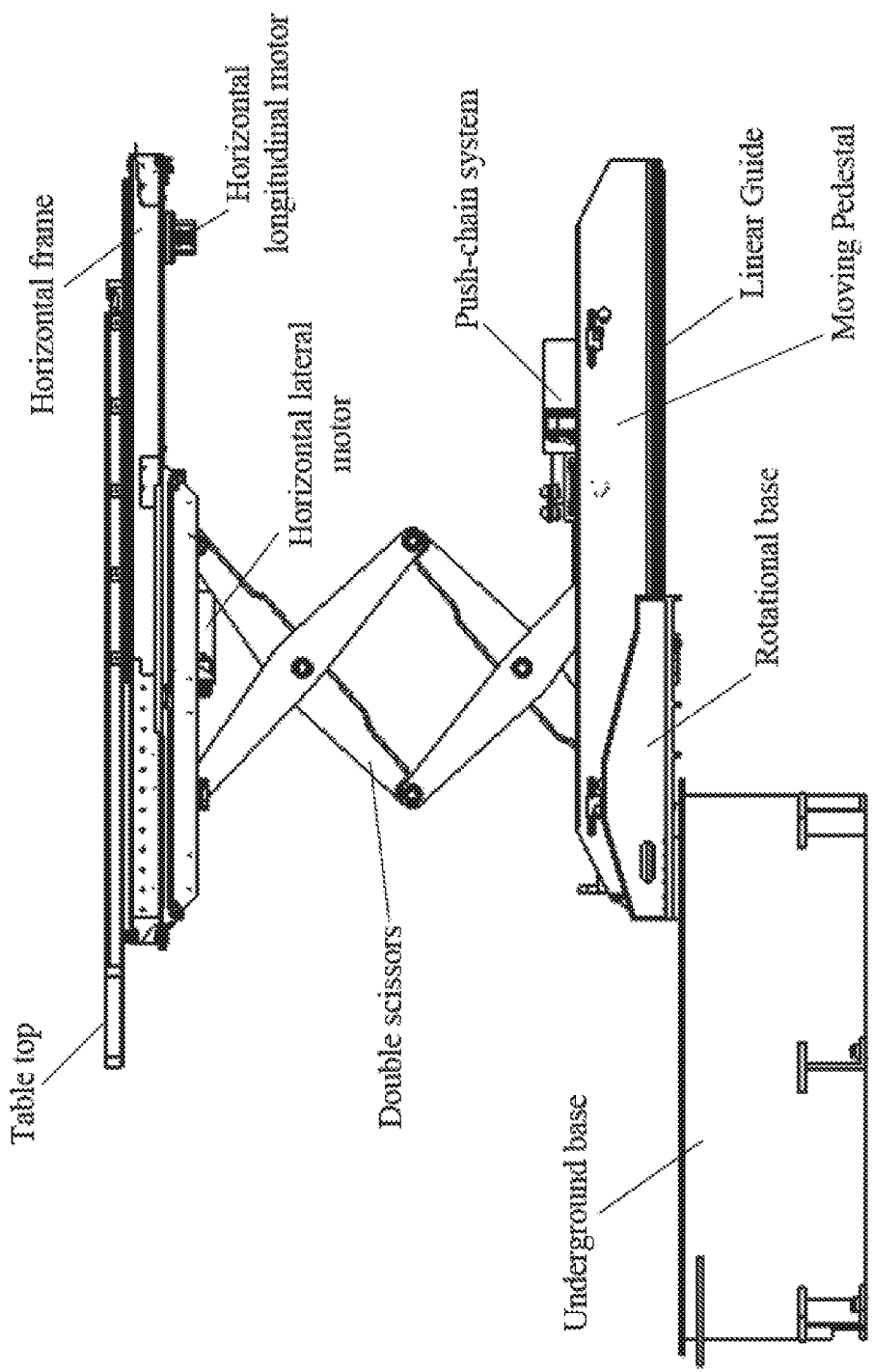
FIG. 16 is a side elevation view of a couch assembly according to some embodiments.
Figure 17:
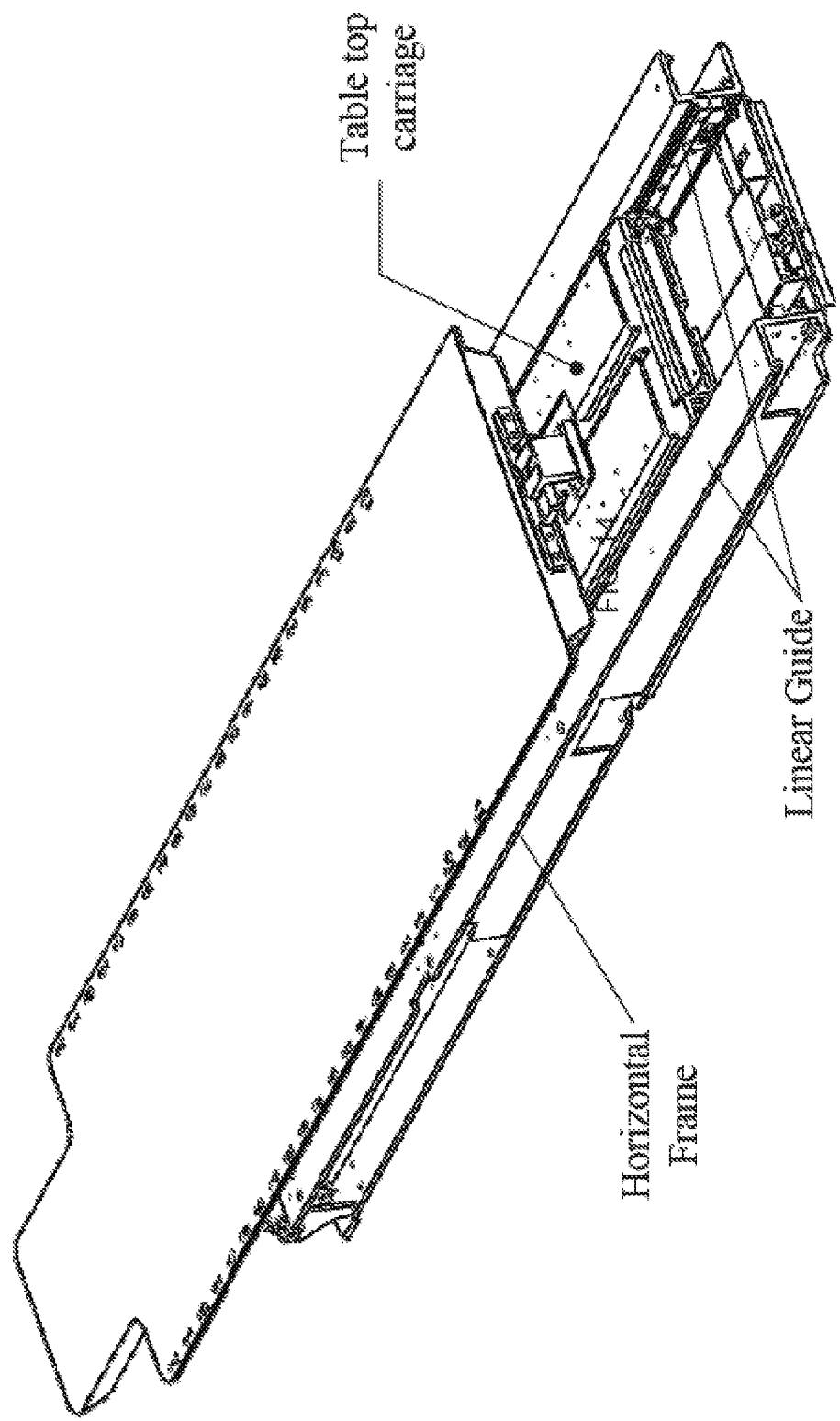
FIG. 17 is a top-side perspective view of a patient support according to some embodiments.
Figure 18:
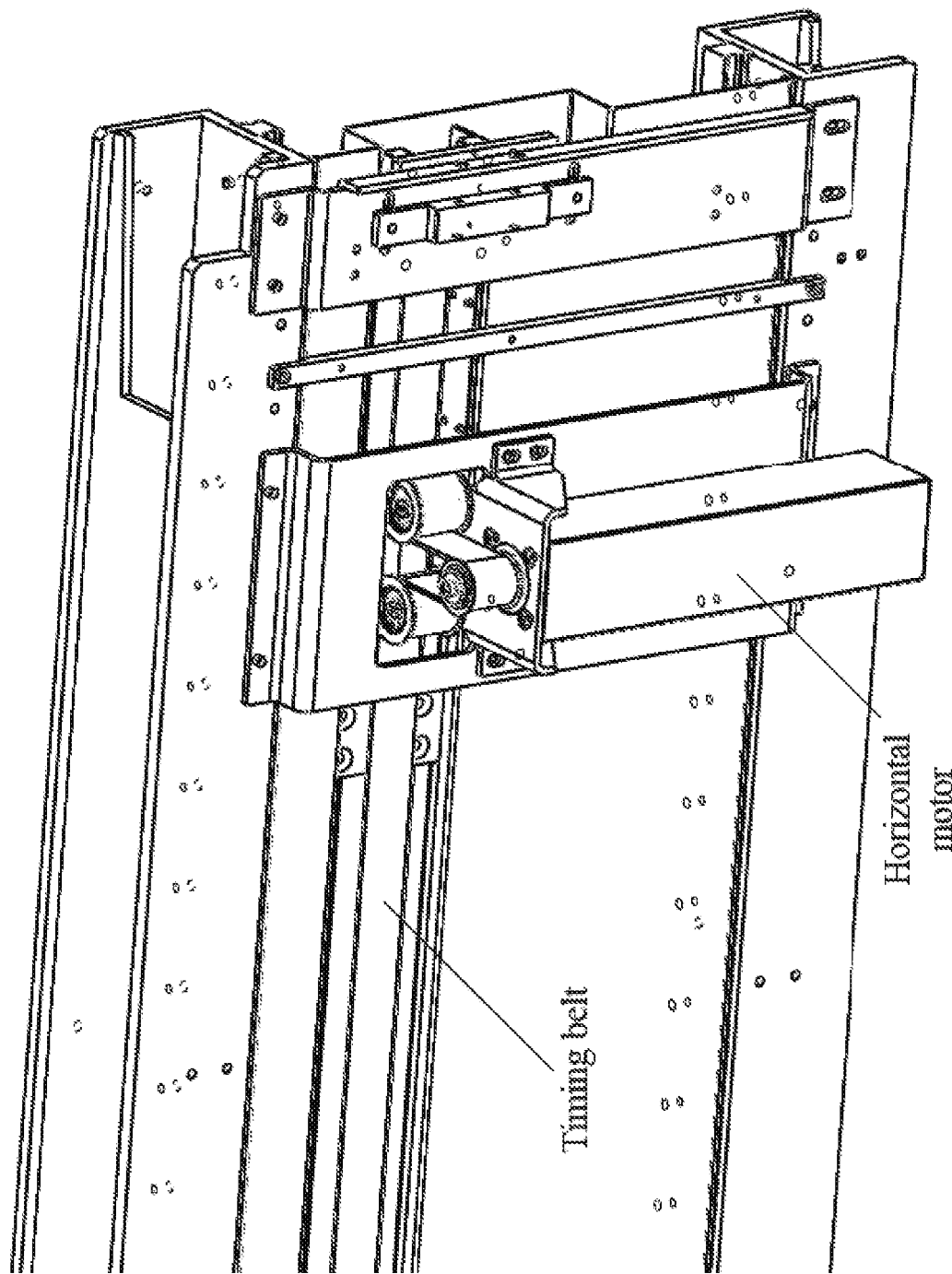
FIG. 18 is a bottom-side perspective view of a patient support according to some embodiments.
Figure 19:
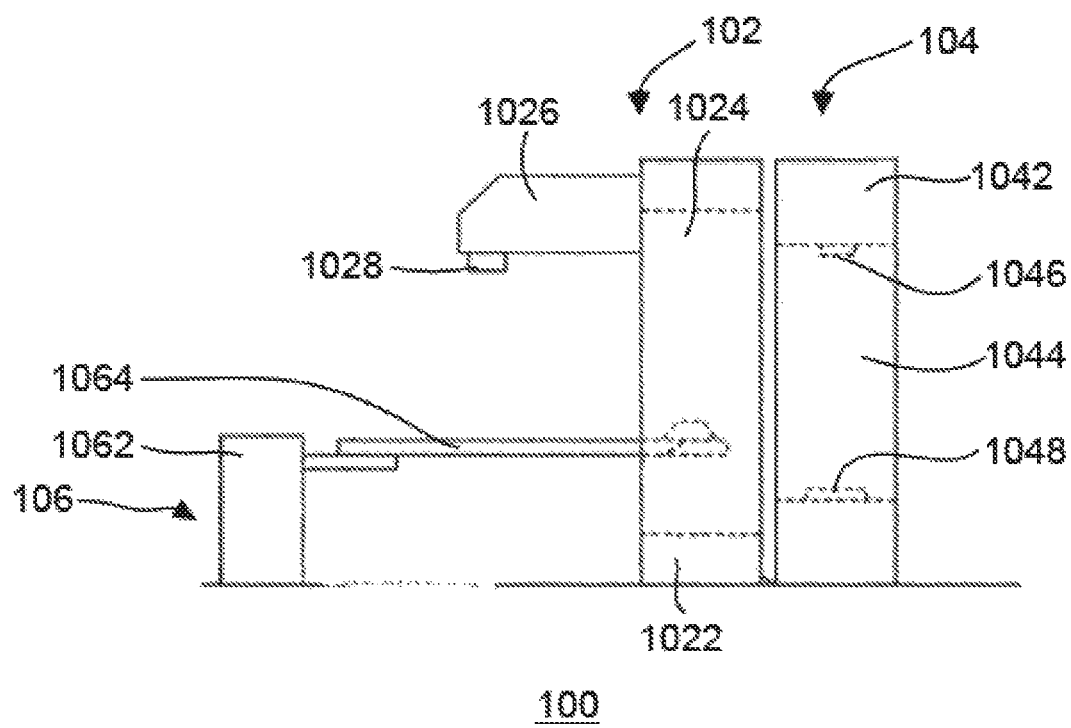
FIG. 19 schematically illustrates a combined medical apparatus.
Figure 20:
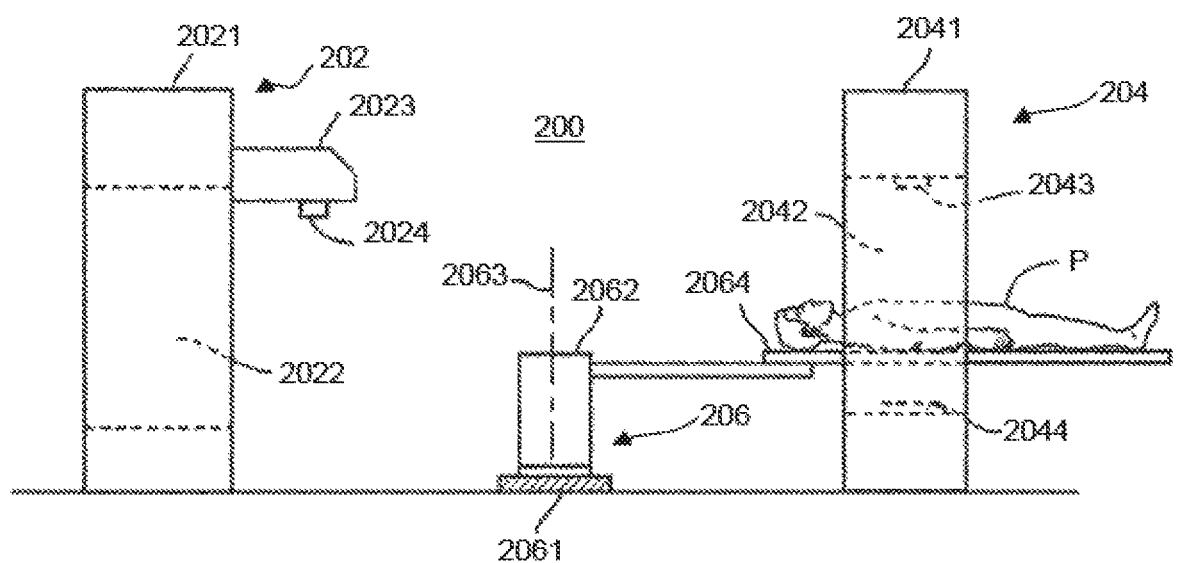
FIG. 20 schematically illustrates a combined medical apparatus.

In order to completely scan a known target area, the patient support 908 is required to move in the first horizontal direction such that the predetermined scan area (generally, an expected length of the scan area will be between 600-900 mm) could be completely scanned by the imaging plane, for example as shown in FIG. 14. If the target area is not entirely known, the predetermined scan area may be longer. For example, the length of a full-length scan could be predetermined as 2 meters and the length of a half-length scan could be predetermined as 1 meter. Since the couch assembly 900 is located on the same side of the radiation therapy assembly 600, the patient support 908 is required to move through the first through-hole 510 of the gantry 500 in order to acquire an image. In comparison to an independent imaging device such as an independent CT imaging device, it is necessary for the patient support 908 to allow a longer range of movement in the first horizontal direction.

After imaging, a patient on the patient support 908 is moved from the imaging position to the radiation position, i.e., moving the patient support 908 until the isocenter of the radiation therapy assembly 600 is aligned with the target area determined by the imaging assembly 700. During radiotherapy, the height adjustment mechanism 9046 may be adjusted such that the patient support 908 is at an appropriate height considering the different depths of target areas of different patients or the different depths of different target areas of a single patient. Further, in order to ensure that the beam from the radiation head 604 radiates the target area from different directions specified by the treatment plan system, the patient support 908 could be rotated about the center of the base 9022 to a predetermined angle.

Considering the length of the arm 602, the longitudinal length of the gantry 500, and other possible scan conditions, the movable distance for the patient support 908 of the couch assembly 900 from a first position where the patient is to be imaged by the imaging assembly 700 to the second position where the patient is to be radiated by the radiation therapy assembly 600 may be between 1900-4600 mm, 1900-4000 mm, 1900-3500 mm, or 1900-3200 mm. If the scan length is predetermined, the movable distance for the patient support 908 from the first position to the second position may be generally equal to the sum of the distance between the isocenter of the radiation therapy assembly 600 and the imaging plane of the imaging assembly 700 and the predetermined scan length.

In a radiotherapy mode, and according to some embodiments: (1) the patient support 908 is movable in the first horizontal direction; (2) the patient support 908 is movable in the second horizontal direction perpendicular to the first horizontal direction; (3) the patient support 908 is adjustable in the vertical direction; and (4) the patient support 908 is rotatable about a vertical axis.

In an the imaging mode, and according to some embodiments: (1) the patient support 908 is movable in the first horizontal direction; (2) the patient support 908 is movable in the second horizontal direction perpendicular to the first horizontal direction; and (3) the patient support 908 is adjustable in the vertical direction.

If the first support plate 9024 of the first support assembly 902, the second support assembly 904, and the third support assembly 906 in the exemplary embodiment is regarded as one new assembly, this new assembly is rotatably supported on the base 9022 on the one hand and, on the other hand, supports the patient support 908 such that the patient support 908 is movable in the first horizontal direction. The above-described motions of the patient support 908 under the radiotherapy mode and the imaging mode can be achieved by configuring this assembly to be movable along the first horizontal direction, the second horizontal direction perpendicular to the first horizontal direction and the vertical direction. Embodiments may employ and systems and structures to implement the above-mentioned movements.

FIGS. 15 through 18 illustrate specific mechanisms to implement the above-described movements according to some embodiments. Patient support 908 (i.e., table top) is movable in a horizontal lateral direction using a horizontal lateral motor, and in a horizontal longitudinal direction along linear guides of a table top carriage using a horizontal longitudinal motor driving a timing belt. Rotational motion is provided by the rotational base, and linear motion of the pedestal is provided by a push-chain system and a linear guide. The illustrated double scissors provide vertical motion of the table top with respect to the pedestal.

Embodiments may comprise a couch assembly comprising a base, a support assembly, and a patient support, in which the support assembly is rotatably supported on the base, the patient support is mounted on the support assembly and movable along a first horizontal direction, and the support assembly is configured to be movable along the first horizontal direction, a second horizontal direction perpendicular to the first horizontal direction, and an upright direction. Such an embodiment may be the radiation therapy medical apparatus 10, 20, comprising a gantry 500, a radiation therapy assembly 600 fixed to one side of the gantry 500, and an imaging assembly 700 fixed to the other side of the gantry 500. The imaging assembly 700 is away from the couch assembly 900 with respect to the radiation therapy assembly 600, and, during imaging by the imaging assembly 700, the support assembly is configured to be movable toward the imaging assembly 700 along the first horizontal direction and the patient support is also movable toward the imaging assembly 700 along the first horizontal direction. To move the patient from a first position of imaging by the imaging assembly 700 to a second position of radiation by the radiation therapy assembly 600, a distance of the patient support 908 movable with respect to the base 9022 may be between 1900 and 4600 mm, 1900 and 4000 mm, 1900 and 3500 mm or 1900 and 3200 mm.

What is claimed is:

1. A radiation therapy apparatus, comprising:
   a base;
   a cylinder-shaped gantry having a longitudinal axis along an axial direction of the gantry,
   wherein the gantry rotates around the longitudinal axis and is supported by the base;
   a radiation therapy assembly comprising a radiation head, wherein the radiation head is fixed to a first position on a first side of the gantry;
   an imaging assembly mounted to a second side of the gantry opposite to the first side and configured to act as a first counterbalance to a weight of the radiation therapy assembly; and
   a second counterbalance fixed to the second side of the gantry, and configured to cooperate with the imaging assembly to inhibit the gantry from tipping at least partially off the base.

2. The radiation therapy apparatus of claim 1, wherein the second counterbalance is oppositely offset from a direction of the radiation head with respect to a rotation axis of the gantry.

3. The radiation therapy apparatus of claim 1, wherein the second counterbalance is fixed to a second position on the second side of the gantry, wherein the second position is peripherally offset from the first position by 180 degrees.

4. The radiation therapy apparatus of claim 1, wherein the radiation therapy assembly comprises a portal imaging device which is coupled to the first side of the gantry opposite to the radiation head.

5. The radiation therapy apparatus of claim 4, wherein the second counterbalance is fixed to a second position of the second side of the gantry, and the second position is opposite to the portal imaging device on the first side of the gantry.

6. The radiation therapy apparatus of claim 1, further comprising a secondary imaging assembly coupled to the first side of the gantry, the secondary imaging assembly comprising an x-ray source and a detector disposed opposite to the x-ray source.

7. The radiation therapy apparatus of claim 1, wherein a distance from an isocenter of the radiation therapy assembly to an imaging plane of the imaging assembly is between 1300 mm and 2600 mm, between 1300 mm and 2300 mm, between 1300 mm and 2000 mm, or between 1300 mm and 1700 mm.

8. The radiation therapy apparatus of claim 1, wherein the gantry defines a first through-hole, and wherein a length of the first through-hole is between 400 mm and 800 mm, or between 500 mm and 700 mm.

9. The radiation therapy apparatus of claim 1, further comprising a couch assembly, the couch assembly comprising a patient support for supporting a patient,
   wherein a distance to move the patient support from a third position at which a patient is to be imaged by the imaging assembly to a fourth position at which the patient is to be radiated by the radiation therapy assembly is between 1900 mm and 4600 mm, between 1900 mm and 4000 mm, between 1900 mm and 3500 mm, or between 1900 mm and 3200 mm.

10. A radiation therapy apparatus, comprising:
    a base;
    a cylinder-shaped gantry having a longitudinal axis along an axial direction of the gantry,
    wherein the gantry rotates around the longitudinal axis and is supported by the base;
    a radiation therapy assembly, comprising a radiation head, wherein the radiation head is fixed to a first side of the gantry;
    an imaging assembly mounted to a second side of the gantry opposite to the first side and configured to act as a first counterbalance to a weight of the radiation therapy assembly; and
    a second counterbalance fixed to the second side of the gantry, and configured such that a projection of a center of mass of the second counterbalance, the gantry, the radiation therapy assembly, and the imaging assembly falls between supporting points at which the base supports the gantry.

11. The radiation therapy apparatus of claim 10, further comprising a secondary imaging assembly coupled to the first side of the gantry.

12. The radiation therapy apparatus of claim 11, wherein a distance between an imaging plane of the secondary imaging assembly and an isocenter of the radiation therapy assembly is between 500 mm and 1600 mm.

13. The radiation therapy apparatus of claim 11, further comprising a couch assembly comprising a patient support, wherein a distance to move the patient support from a first position at which a patient is to be imaged by the secondary imaging assembly to a second position at which the patient is to be radiated by the radiation therapy assembly is between 1100 mm and 3600 mm, 1100 mm and 2500 mm, or 1100 mm and 2200 mm.

14. The radiation therapy apparatus of claim 10, wherein a distance between an imaging plane of the imaging assembly and an isocenter of the radiation therapy assembly is between 1300 mm and 2600 mm.

15. The radiation therapy apparatus of claim 10, further comprising a couch assembly comprising a patient support, wherein a distance to move the patient support from a first position at which a patient is to be imaged by the imaging assembly to a second position at which the patient is to be radiated by the radiation therapy assembly is between 1900 mm and 4600 mm, 1900 mm and 3500 mm or 1900 mm and 3200 mm.

* * * * *